US006773880B2

(12) United States Patent
Sampson et al.

(10) Patent No.: US 6,773,880 B2
(45) Date of Patent: Aug. 10, 2004

(54) STREPTOCOCCUS PNEUMONIALE 37-KDA SURFACE ADHESION A PROTEIN

(75) Inventors: Jacquelyn Sampson, College Park, GA (US); Harold Russell, Efland, NC (US); Jean A. Tharpe, Lithonia, GA (US); Edwin W. Ades, Atlanta, GA (US); George M. Carlone, Stone Mountain, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 553 days.

(21) Appl. No.: 09/754,809

(22) Filed: Jan. 3, 2001

(65) Prior Publication Data

US 2003/0105307 A1 Jun. 5, 2003

Related U.S. Application Data

(60) Division of application No. 09/221,753, filed on Dec. 28, 1998, now Pat. No. 6,217,884, which is a division of application No. 08/715,131, filed on Sep. 17, 1996, now Pat. No. 5,854,416, which is a continuation-in-part of application No. 08/222,179, filed on Apr. 4, 1994, now abandoned, which is a continuation-in-part of application No. 07/791,377, filed on Sep. 17, 1991, now Pat. No. 5,422,427.

(51) Int. Cl.[7] .................................................. C12Q 1/68
(52) U.S. Cl. ....................... 435/6; 536/23.7; 536/24.32; 536/24.33
(58) Field of Search .......................... 435/6; 536/23.7, 536/24.32, 24.33

(56) References Cited

U.S. PATENT DOCUMENTS

| 4,762,713 A | 8/1988 | Anderson |
| 4,789,735 A | 12/1988 | Frank et al. |
| 4,894,362 A | 1/1990 | Yamaguchi et al. |
| 5,037,760 A | 8/1991 | Smith et al. |
| 5,130,417 A | 7/1992 | Stanley et al. |
| 5,422,427 A | 6/1995 | Russell et al. |
| 5,854,416 A | 12/1998 | Sampson et al. |

FOREIGN PATENT DOCUMENTS

| EP | 0206 852 A1 | 12/1986 |
| EP | 0 429 816 A1 | 6/1991 |

OTHER PUBLICATIONS

Sampson, et al., "Immonulogic Characterization of a Monoclonal Antibody to *Streptococcus Pneumoniae* Pneumococcal Surface Adhesin A (PsaA) Protein," Centers for Disease Control & Prevention, Atlanta, Ga 30333.

Novak, et al., "Penicillin tolerance genes of *Streptococcus pneumoniae*: the ABC–type manganese permease complex Psa," *Molecular Microbiology*, 29:1285–1296 (1998).

Lawrence, et al., "The crystal structure of pneumococcal surface antigen PsaA reveals a metal–binding site and a novel structure for a putative ABC–type binding protein," *Structure*, 6:1553–1561, (Dec. 1998).

Amit, et al., "Three–Dimensional Structure of a Antigen–Antibody Complex at 2.8 Angstrom Resolution," *Science*, 233:747–753 (Apr. 1986).

Kolenbrander, et al., "Nucleotide Sequence of the *Streptococcus gordonii* PK488 Coaggregation Adhesin Gene, scaA, and ATP–Binding Cassette," *Infection and Immunity*, 62(10):4469–4480, (Oct. 1994).

Talkington, et al., "A 43–Kilodalton Pneumococcal Surface Protein, PspA: Isolation, Protective Abilities, and Structural Analysis of the Amino–Terminal Sequence," *Infection and Immunity*, 59(4):1285–1289, (Apr. 1991).

Sampson, et al., "Molecular Cloning of the Gene Encoding the 37–Kilodalton Protein of *Streptococcus pneumoniae*," Abstracts of the 91st General Meeting of the Am. Society for Microbiology Annual Meeting; p. 97, (1991).

Russell, et al., "Assay for Antibodies Against a Species–Specific *Streptococcus Pneumoniae* Antigen in Patients with Pneumococcal Disease," Abstracts of the 91st General Meeting of the Am. Society for Microbiology; p. 434 (1991).

(List continued on next page.)

*Primary Examiner*—Jennifer E. Graser
(74) *Attorney, Agent, or Firm*—Needle & Rosenberg, P.C.

(57) ABSTRACT

The invention provides a nucleic acid encoding the 37-kDa protein from *Streptococcus pneumoniae*. Also provided are isolated nucleic acids comprising a unique fragment of at least 10 nucleotides of the 37-kDa protein. The invention also provides purified polypeptides encoded by the nucleic acid encoding the 37-kDa protein from and the nucleic acids comprising a unique fragment of at least 10 nucleotides of the 37-kDa protein. Also provided are antibodies which selectively binds the polypeptides encoded by the nucleic acid encoding the 37-kDa protein and the nucleic acids comprising a unique fragment of at least 10 nucleotides of the 37-kDa protein. Also provided are vaccines comprising immunogenic polypeptides encoded by the nucleic acid encoding the 37-kDa protein and the nucleic acids comprising a unique fragment of at least 10 nucleotides of the 37-kDa protein. Further provided is a method of detecting the presence of *Streptococcus pneumoniae* in a sample comprising the steps of contacting a sample suspected of containing *Streptococcus pneumoniae* with nucleic acid primers capable of hybridizing to a nucleic acid comprising a portion of the nucleic acid encoding the 37-kDa protein, amplifying the nucleic acid and detecting the presence of an amplification product, the presence of the amplification product indicating the presence of *Streptococcus pneumoniae* in the sample. Further provided are methods of detecting the presence of *Streptococcus pneumoniae* in a sample using antibodies or antigens, methods of preventing and treating *Streptococcus pneumoniae* infection in a subject.

1 Claim, No Drawings

OTHER PUBLICATIONS

Russell, et al., Isolation and Purification of a Species–Specific *Streptococcus pneumoniae* Protein Antigen by Isoelectric focusing, Abstracts of the Annual Meeting—1990 of the Am. Society for Microbiology Annual Meeting; p. 436 (1990).

Ganeshkumar, et al., "Nucleotide Sequence of a Gene Coding for a Saliva–Binding Protein (SsaB) from *Streptococcus sanguis* 12 and Possible Role of the Protein in Coaggregation with Actinomyces," *Infection and Immunity*, 59(3):1093–1099, (Mar. 1991).

Russell, et al., "Investigation of *Streptococcus Pneumoniae* Components for Immunodiagnostic Markers," Abstracts of the 89$^{th}$ Annual Meeting of the Am. Society for Microbiology; p. 489 (1989).

Van de Wijgert, et al., "Immunogenicity of *Streptococcus Pneumoniae* Type 14 Capsular Polysaccharide: Influence of Carriers and Adjuvants on Isotype Distribution," *Infection & Immunity*, 59(8):2750–2757 (Aug. 1991).

Audibert and Lise, "Adjuvants: Current Status, Clinical Perspectives and Future Prospects," *Immunology Today*, 14(6):281–284 (1993).

Vella, et al., "Immunogenicity of Conjugate Vaccines Consisting of Pneumococcal Capsular Polysaccharide Types . . . ," *Infection and Immunity*, 60(12):4977–4983 (Dec. 1992).

Green, et al., "Evaluation of Mixtures of Purified Haemophilus Influenzae Outer Membrane Proteins . . . " *Infection and Immunity*, 61(5):1950–1957 (May 1993).

Bixler and Atassi, "B Cell Recognition of Protein Antigens—Perspectives From The Submolecular Level." *In: Synthetic Vaccines*, (Arnon, ed.) 1:39—71, CRC Press, Inc., Boca Raton, FL. (1987).

Berry and Paton, "Sequence Heterogeneity of PsaA, a 37–Kilodalton Putative Adhesin Essential for Virulence of *Streptococcus pneumoniae*," *Infection and Immunity*, 64(12):5255–5262 (Dec. 1996).

Russell, et al., "Monoclonal Antibody Recognizing a Species–Specific Protein from *Streptococcus pneumoniae*," *J. Clin. Microbiol.* 28:2191–2195, (Oct. 1990).

Briles, D.E., et al., "Antipneumococcal Effects of C–Reactive Protein and Monoclonal Antibodies to Pneumococcal Cell Wall and Capsular Antigens," *Infection and Immunity*, 57(5):1457–1464. (May 1989).

Fenno, et al., "Nucleotide Sequence Analysis of a Type 1 Fimbral Gene of *Streptococcus sanguis* FW213," *Infection and Immunity*, 57(11):3527–3533, (Nov. 1989).

Advertisement offering custom DNA/Peptides; total gene synthesis. *Science*, 240:362, (1988).

Fives–Taylor, et al., "Expression of *Streptococcus sanguis* Antigens in *Escherichia Coli:* Cloning of a Structural Gene for Adhesion Fimbriae," *Infection and Immunity*, 55(1):123–128, (Jan. 1987).

Clark–Lewis, et al., "Automated Chemical Synthesis of a Protein Growth Factor for Hemopoietic Cells, Interleukin–3," *Science*, 231:134–139, (Jan. 1986).

Caruthers, et al., "Gene Synthesis Machines: DNA Chemistry and Its Uses," *Science*, 230:281–285, (Oct. 1985).

Tharpe and Russell, "Purification and Seroreactivity of Pneumococcal Surface Adhesin A (PsaA)," *Clinical and Diagnostic Laboratory Immunology*, 3(2):227–229, (Mar. 1996).

Sampson, et al., "Cloning and Nucleotide Sequence Analysis of psaA, the *Streptococcus pneumoniae* Gene Encoding a 37–Kilodalton Protein Homologous to Previously Reported Streptococcus sp. Adhesins," *Infection and Immunity*, 62(1):319–324, (Jan. 1994).

Sampson, et al., "Conservation of the 37–kDa Protein Gene among *Streptococcus pneumoniae* Serotypes," Interscience Conference of Antimicrobial Agents and Chemotherapy (ICAAC), (Sep. 17, 1995).

Yother and Briles, "Structural Properties and Evolutionary Relationships of PspA, a Surface Protein of *Streptococcus pneumoniae*, as Revealed by Sequence Analysis," *J. of Bacteriology*, 174(2):601–609, (Jan. 1992).

Waltman, et al., "Variation in the molecular weight of PspA (pneumococcal surface of protein A) among *Streptococcus pneumoniae*," *Microbial Pathogenesis*, 8(1):61–69 (Jan. 1990).

Talkington, et al., "The 37–kDa Protein of *Streptococcus pneumoniae* Protects Mice against Fatal Challenge," Abstracts of the General Meeting of the American Society for Microbiology, New Orleans, Louisiana, cover page and E–29 on p. 149 (1992).

McDaniel, L.S., et al., "PspA, a Surface Protein of *Streptococcus pneumoniae*, Is Capable of Eliciting Protection against Pneumococci of More Than One Capsular Type," *Infection and Immunity*, 59(1):222–228, (Jan. 1991).

McDaniel, L.S., et al., "Use of Insertional Inactivation To Facilitate Studies of Biological Properties of Pneumococcal Surface Protein A (PspA)," *J. Experimental Medicine*, 165:381–394, (Feb. 1987).

STREPTOCOCCUS PNEUMONIALE 37-KDA SURFACE ADHESION A PROTEIN

This application is a divisional of and claims the benefit of priority from, U.S. Ser. No. 09/221,753, filed Dec. 28, 1998 now U.S. Pat. No. 6,217,884, which is a divisional of U.S. Ser. No. 08/715,131, filed Sep. 17, 1996, now U.S. Pat. No. 5,854,416, which is a continuation-in-part of U.S. Ser. No. 08/222,179, filed Apr. 4, 1994, now abandoned which is a continuation-in-part of U.S. Ser. No. 07/791,377, filed Sep. 17, 1991, now U.S. Pat. No. 5,422,427, which applications are hereby incorporated herein by reference.

BACKGROUND OF THE INVENTION

FIELD OF THE INVENTION

This invention relates to the 37-kDa *Streptococcus pneumoniae* surface adhesin A protein. Specifically, the invention relates to an isolated nucleic acid encoding the 37-kDa protein of *Streptococcus pneumoniae*, to unique fragments of the nucleic acid encoding the 37-kDa protein of *Streptococcus pneumoniae*, and to the polypeptides encoded by those nucleic acids. The invention further relates to antibodies to those polypeptides, and to methods of detecting the presence of *Streptococcus pneumoniae*, methods of preventing *Streptococcus pneumoniae* infection, and methods of treating a *Streptococcus pneumoniae* infection.

BACKGROUND ART

Pneumococcal disease continues to be a leading cause of sickness and death in the United States and throughout the world. Both the lack of efficacy of the currently used polysaccharide vaccines in children under 2 years of age and their variable serotype-specific efficacy among vaccinated individuals, have prompted manufacturers to investigate alternative vaccine formulations that do not require the use of multiple capsular polysaccharides. One current approach under consideration is the use of immunogenic species-common proteins as vaccine candidates. These proteins could be used in combination with other immunogenic proteins or as protein carriers in a protein-polysaccharide or oligosaccharide conjugate vaccine. An effective vaccine that included a common protein could eliminate the need for formulations based on multiple capsular polysaccharides (as in the 23-valent polysaccharide vaccine) by offering a broader range of protection against a greater number of serotypes. Additionally, a protein-based vaccine would be T-cell dependent and provide a memory response, resulting in a more efficacious vaccine.

Of the reported pneumococcal proteins, only pneumolysin and the pneumococcal surface protein A (PspA) have been extensively examined for their suitability as vaccine candidates. While both have been shown to be partially protective in mice (Paton et al. 1983. "Effect of immunization with pneumolysin on survival time of mice challenged with *Streptococcus pneumoniae*." Infect. Immun. 40:548–552 and McDaniel et al. 1991. "PspA, a surface protein of *Streptococcus Pneumoniae*, is capable of eliciting protection against pneumococci of more than one capsular type." Infect. Immun. 59:222–228), there are disadvantages to their use as vaccine immunogens. Pneumolysin, although well conserved among pneumococci, has been shown to have strong toxic effects in its native state (AlonsoDeVelasco et al. 1995. "*Streptococcus pneumoniae*: Virulence factors, pathogenesis, and vaccines." Microbiol. Rev. 59:591–603). Recombinant derivatives of reduced toxicity have been produced, and while they show promise in animal protection studies (Alexander et al. 1994. "Immunization of mice with pneumolysin toxoid confers a significant degree of protection against at least nine serotypes of *Streptococcus pneumoniae*. Infect. Immun. 62:5683–5688) the problem of maintaining maximal immunogenicity and eliminating toxicity to humans is still in question. PspA, on the other hand, is serologically and structurally heterogeneous. (Crain et al. 1990. "Pneumococcal surface protein A (PspA) is serologically highly variable and is expressed by all clinically important capsular serotypes of *Streptococcus pneumoniae*." Infect. Immun. 58:3293–3299). Its use in vaccine formulations would require multiple PspA types, thus increasing the complexity of vaccine preparation.

An immunogenic species-common protein has been identified from *Streptococcus pneumoniae*. (Russell et al. 1990. "Monoclonal antibody recognizing a species-specific protein from *Streptococcus pneumoniae*." J. Clin. Microbiol. 28:2191–2195 and U.S. Pat. No. 5,422,427 in which the 37-kDa protein is referred to as pneumococcal fimbrial protein A). The 37-kDa *S. pneumoniae* protein has been the focus of several studies and has been designated pneumococcal surface adhesin protein A (PsaA). Immunoblot analysis studies using anti-PsaA monoclonal antibody showed that PsaA is common to all 23 pneumococcal vaccine serotypes (Russell et al. 1990). Enzyme-linked-immunosorbent assay studies have indicated that patients with pneumococcal disease show an antibody increase in convalescent-phase serum to PsaA compared with acute-phase serum antibody levels (Tharpe et al. 1995. "Purification and seroreactivity of pneumococcal surface adhesin A (PsaA)." Clin. Diagn. Lab. Immunol. 3:227–229 and Tharpe et al. 1994. "The utility of a recombinant protein in an enzyme immunoassay for antibodies against *Streptococcus pneumoniae*." abstr. V-2, p. 617. 1994. American Society for Microbiology, Washington, D.C.). Additionally, a limited in vivo protection study showed that antibodies to the 37-kDa protein protect mice from lethal challenge (Talkington et al. 1996. "Protection of mice against fatal pneumococcal challenge by immunization with pneumococcal surface adhesin A (PsaA)." Microbial Pathogenesis 21:17–22).

The gene encoding PsaA from *S. pneumoniae* strain R36A (an unencapsulated strain) has been cloned in *Escherichia coli* and sequenced, but this serotype does not contain a 37kDa protein encoding nucleic acid that is highly conserved among the various serotypes. (Sampson et al. 1994. "Cloning and nucleotide sequence analysis of psaA, the *Streptococcus pneumoniae* gene encoding a 37-kilodalton protein homologous to previously reported Streptococcus sp. adhesins." Infect. Immun. 62:319–324). This particular nucleic acid and polypeptide, therefore, are of limited value for use as diagnostic reagents, in infection prevention, in infection treatment, or in vaccine development.

Sequence conservation is a necessary requirement for a candidate species-common vaccine. At present, there are no studies that have investigated the sequence conservation of the psaA gene among pneumococcal types, specifically among encapsulated pneumococci which cause the vast majority of serious disease. Therefore, a need exists to investigate the conservation of the gene in order to provide a polypeptide which can serve as a vaccine for multiple strains of *Streptococcus pneumoniae*. The present invention fulfills that need by analyzing psaA genes from the 23 serotypes in the 23-valent polysaccharide vaccine and by providing a polypeptide and antibodies to that polypeptide which are conserved among the *S. pnuemoniae* serotypes and which confer protection to *Streptococcus pneumoniae* infection.

SUMMARY OF THE INVENTION

In accordance with the purpose(s) of this invention, as embodied and broadly described herein, this invention, in one aspect, relates to an isolated nucleic acid encoding the 37-kDa protein of *Streptococcus pneumoniae* as set forth in the Sequence Listing as SEQ ID NO:2. The invention also provides unique fragments of at least 10 nucleotides of the nucleic acid set forth in the Sequence Listing as SEQ ID NO:1, which can be used in methods to detect the presence of *Streptococcus pneumoniae* in a sample and as immunogenic vaccines.

The invention further provides a purified polypeptide encoded by the nucleic acid encoding the 37-kDa protein of *Streptococcus pneumoniae* as set forth in the Sequence Listing as SEQ ID NO:1, which can be used as immunogenic vaccines.

In another aspect, the invention provides purified antibodies which bind to the 37-kDa protein of *Streptococcus pneumoniae* or fragments thereof These antibodies can be used in methods to detect the presence of *Streptococcus pneumoniae* in a sample and in therapeutic and prophylactic methods.

The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Throughout this application, various publications are referenced. The disclosures of these publications in their entireties are hereby incorporated by reference into this application in order to more fully describe the state of the art to which this application pertains.

DETAILED DESCRIPTION OF THE INVENTION

The present invention may be understood more readily by reference to the following detailed description of the preferred embodiments of the invention and the Examples included therein.

Before the present compounds and methods are disclosed and described, it is to be understood that this invention is not limited to specific proteins, specific methods, or specific nucleic acids, as such may, of course, vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise. Thus, for example, reference to "a nucleic acid" includes multiple copies of the nucleic acid and can also include more than one particular species of nucleic acid molecule.

Nucleic Acids

In one aspect, the invention provides an isolated nucleic acid encoding the 37-kDa protein of *Streptococcus pneumoniae* as set forth in the Sequence Listing as SEQ ID NO:2. The term "isolated" refers to a nucleic acid which is essentially separated from other genes that naturally occur in *S. pneumoniae*. In one embodiment, the present invention provides an isolated nucleic acid encoding the 37-kDa protein of *Streptococcus pneumoniae* wherein the nucleic acid is the nucleic acid set forth in the Sequence Listing as SEQ ID NO:1.

The nucleic acids of the present invention can include the positive and/or negative RNA strand as well as the sense and/or nonsense DNA strand, or any combinations thereof These nucleic acids include the genomic DNA fragment encoding the 37-kDa protein and any subgenomic nucleic acids, including DNA and RNA, in the organism encoding all, or a fragment of the 37-kDa protein. The nucleic acid can also be modified, such as nucleic acids containing methylated bases.

This nucleic acid can comprise the coding sequence for the 37-kDa protein itself, or the coding sequence with the gene's upstream and downstream regulatory sequences, or any combination thereof This nucleic acid can, for example, comprise a DNA and include its own promoter, or another promoter can be operatively linked to the nucleic acid such that the coding sequence of the 37-kDa protein is expressed. Alternatively, the nucleic acid can comprise an RNA such that the RNA is translated and the resulting polypeptide comprises the 37-kDa protein. Therefore sequences normally found associated with the 37-kDa protein coding sequence, such as the promoter, and the translation signals, can be substituted, deleted, or modified.

An isolated nucleic acid comprising a unique fragment of at least 10 nucleotides of the nucleic acid set forth in the Sequence Listing as SEQ ID NO:1 is also provided. Unique fragments, as used herein means a nucleic acid of at least 10 nucleotides that is not identical to any other known nucleic acid sequence. Examples of the sequences of at least 10 nucleotides that are unique to the nucleic acid set forth in the Sequence Listing as SEQ ID NO:1 can be readily ascertained by comparing the sequence of the nucleic acid in question to sequences catalogued in GenBank, or any other sequence database, using computer programs such as DNASIS (Hitachi Engineering, Inc.) or Word Search or FASTA of the Genetics Computer Group (GCG) (Madison, Wis.), which search the catalogued nucleotide sequences for similarities to the nucleic acid in question. If the sequence does not match any of the known sequences, it is unique. For example, the sequence of nucleotides 1–10 can be used to search the databases for an identical match. If no matches are found, then nucleotides 1–10 represent a unique fragment. Next, the sequence of nucleotides 2–11 can be used to search the databases, then the sequence of nucleotides 3–13, and so on up to nucleotides 1320 to 1330 of the sequence set forth in the Sequence Listing as SEQ ID NO:1. The same type of search can be performed for sequences of 11 nucleotides, 12 nucleotides, 13 nucleotides, etc. The possible fragments range from 10 nucleotides in length to 1 nucleotide less than the sequence set forth in the Sequence Listing as SEQ ID NO:1. These unique nucleic acids, as well as degenerate nucleic acids can be used, for example, as primers for amplifying nucleic acids from other strains of *Streptococcus pneumoniae* in order to isolate allelic variants of the 37-kDa protein, or as primers for reverse transcription of 37-kDa protein RNA, or as probes for use in detection techniques such as nucleic acid hybridization. One skilled in the art will appreciate that even though a nucleic acid of at least 10 nucleotides is unique to a specific gene, that nucleic acid fragment can still hybridize to many other nucleic acids and therefore be used in techniques such as amplification and nucleic acid detection.

Also provided are nucleic acids which encode alelic variants of the 37-kDa protein of *S. pneumoniae* set forth in the Sequence Listing as SEQ ID NO:2, and those proteins. As used herein, the term "alelic variations" or "alelic variants" is used to describe the same, or similar 37-kDa pneumococcal surface adhesin proteins that are diverged from the 37-kDa *Streptococcus pneumoniae* protein set forth in the Sequence Listing as SEQ ID NO:2 by less than 15% in their corresponding amino acid identity. In another embodiment, these allelic variants are less than 10% divergent in their corresponding amino acid identity. In another embodiment, these allelic variants are less than 7% divergent in their corresponding amino acid identity. In another embodiment, these allelic variants are less than 5% divergent in their corresponding amino acid identity. In another embodiment, these allelic variants are less than 3% divergent in their corresponding amino acid identity. In another embodiment, these allelic variants are less than 2% divergent in their corresponding amino acid identity. In yet another embodiment, these allelic variants are less than 1% divergent in their corresponding amino acid identity. These amino acids can be substitutions within the amino acid sequence set forth in the Sequence Listing as SEQ ID NO:2, they can be deletions from the amino acid sequence set forth in the Sequence Listing as SEQ ID NO:2, and they can be additions to the amino acid sequence set forth in the Sequence Listing as SEQ ID NO:2.

The homology between the protein coding region of the nucleic acid encoding the allelic variant of the 37-kDa protein is preferably less than 20% divergent from the region of the nucleic acid set forth in the Sequence Listing as SEQ ID NO:1 encoding the 37-kDa protein. In another embodiment, the corresponding nucleic acids are less than 15% divergent in their sequence identity. In another embodiment, the corresponding nucleic acids are less than 10% divergent in their sequence identity. In another embodiment, the corresponding nucleic acids are less than 7% divergent in their sequence identity. In another embodiment, the corresponding nucleic acids are less than 5% divergent in their sequence identity. In another embodiment, the corresponding nucleic acids are less than 4% divergent in their sequence identity. In another embodiment, the corresponding nucleic acids are less than 3% divergent in their sequence identity. In another embodiment, the corresponding nucleic acids are less than 2% divergent in their sequence identity. In yet another embodiment, the corresponding nucleic acids are less than 1% divergent in their sequence identity. In particular, the nucleic acid variations can create up to about 15% amino acid sequence variation from the protein set forth in the Sequence Listing as SEQ ID NO:2.

One skilled in the art will appreciate that nucleic acids encoding homologs or allelic variants of the 37-kDa protein set forth in the Sequence Listing as SEQ ID NO:2 can be isolated from related gram-positive bacteria in a manner similar to that used to isolate the nucleic acid set forth in the Sequence Listing of the present invention as SEQ ID NO:1. For example, given the sequence of the primers used to amplify the nucleic acid set forth in the sequence listing as SEQ ID NO:1, one can use these or similar primers to amplify a homologous gene from related gram-positive bacteria.

Alternatively, allelic variants can be identified and isolated by nucleic acid hybridization techniques. Probes selective to the nucleic acid set forth in the Sequence Listing as SEQ ID NO:1 can be synthesized and used to probe nucleic acid from the various serotypes of *S. pneumoniae*. High sequence complementarity and stringent hybridization conditions can be selected such that the probe selectively hybridizes to allelic variants of the sequence set forth in the Sequence Listing as SEQ ID NO:1. For example, the selectively hybridizing nuleic acids of the invention can have at least 70%, 80%, 85%, 90%, 95%, 97%, 98% and 99%o complementarity with the segment of the sequence to which it hybridizes. The nucleic acids can be at least 10, 12, 50, 100, 150, 200, 300, 500, 750, or 1000 nucleotides in length. Thus, the nucleic acid can be a coding sequence for the 37-klja protein or fragments thereof that can be used as a probe or primer for detecting the presence of *M. tuberculosis*. If used as primers, the invention provides compositions including at least two nucleic acids which hybridize with different regions so as to amplify a desired region. Depending on the length of the probe or primer, target region can range between 70% complementary bases and full complementarity and still hybridize under stringent conditions. For example, for the purpose of diagnosing the presence of an allelic variant of the sequence set forth in the Sequence Listing as SEQ ID NO:1, the degree of complementarity between the hybridizing nucleic acid (probe or primer) and the sequence to which it hybridizes is at least enough to distinguish hybridization with a nucleic acid from unrelated bacteria. The invention provides examples of nucleic acids unique to SEQ ID NO:1 in the Sequence Listing so that the degree of complementarity required to distinguish selectively hybridizing from nonselectively hybridizing nucleic acids under stringent conditions can be clearly determined for each nucleic acid. One skilled in the art will appreciate that sequences can be added to either one end or both ends of unique fragments, for example, to aid subsequent cloning, expression, or detection of the fragment.

"Stringent conditions" refers to the washing conditions used in a hybridization protocol. In general, the washing conditions should be a combination of temperature and salt concentration chosen so that the denaturation temperature is approximately 5–20° C. below the calculated $T_m$ of the nucleic acid hybrid under study. The temperature and salt conditions are readily determined empirically in preliminary experiments in which samples of reference DNA immobilized on filters are hybridized to the probe or protein coding nucleic acid of interest and then washed under conditions of different stringencies. The $T_m$ of such an oligonucleotide can be estimated by allowing 2° C. for each A or T nucleotide, and 4° C. for each G or C. For example, an 18 nucleotide probe of 50% G+C would, therefore, have an approximate $T_m$ of 54° C.

In another aspect, the present invention provides an isolated nucleic acid comprising the nucleic acid as set forth in the Sequence Listing as SEQ ID NO:3.

In another aspect, the present invention provides an isolated nucleic acid comprising the nucleic acid as set forth in the Sequence Listing as SEQ ID NO:4.

The nucleic acid encoding a 37-kDa protein may be obtained by any number of techniques known to one skilled in the art. One method is to synthesize a recombinant nucleic acid molecule. For example, oligonucleotide synthesis procedures are routine in the art and oligonucleotides coding for a particular protein or regulatory region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins or regulatory regions can be synthesized by first constructing several different double-stranded molecules that code for particular regions of the protein or regulatory region, followed by ligating these DNA molecules together. For example, Cunningham et al. ("Receptor and Antibody Epitopes in Human Growth Hormone Identified by Homolog-Scanning Mutagenesis," *Science*, 243:1330–1336 (1989)), have constructed a synthetic gene encoding the human growth hormone gene by first constructing overlapping and complementary synthetic oligonucleotides and ligating these fragments together. See also, Ferretti, et al. (Proc. Nat. Acad. Sci. 82:599–603 (1986)), wherein synthesis of a 1057 base pair synthetic bovine rhodopsin gene from synthetic oligonucleotides is disclosed. Once the appropriate DNA molecule is synthesized, this DNA can be cloned downstream of a promoter. Techniques such as this are routine in the art and are well documented.

An example of another method of obtaining a nucleic acid encoding a 37-kDa surface adhesin A protein is to isolate that nucleic acid from the organism in which it is found and clone it in an appropriate vector. For example, a DNA or cDNA library can be constructed and screened for the presence of the nucleic acid of interest. The probe used to screen the library can be designed to be selective for the 6B serotype protein. Methods of constructing and screening such libraries are well known in the art and kits for performing the construction and screening steps are commercially available (for example, Stratagene Cloning Systems, La Jolla, Calif.). Once isolated, the nucleic acid can be directly cloned into an appropriate vector, or if necessary, be modified to facilitate the subsequent cloning steps. Such modification steps are routine, an example of which is the addition of oligonucleotide linkers which contain restriction sites to the termini of the nucleic acid. General methods are set forth in Sambrook et al., "Molecular Cloning, a Laboratory Manual," Cold Spring Harbor Laboratory Press (1989).

Yet another example of a method of obtaining a Streptococcal 37-kDa surface adhesin A encoding nucleic acid is to amplify the nucleic acid from the nucleic acids found within the host organism. Amplification procedures are well known to those skilled in the art, for example see Innis et al. "PCR Protocols: A Guide to Methods and Applications" Academic Press, Inc. 1990. An example of amplification of a nucleic acid encoding the 37-kDa protein of *Streptococcus pneumoniae* serotype 6B is discussed in the Example contained herein.

37-kDa Protein

The present invention also provides a purified polypeptide as set forth in the Sequence Listing a SEQ ID NO:2 and a purified polypeptide encoded by a nucleic acid comprising a unique fragment of at least 10 nucleotides of SEQ ID NO:1. The protein can be used as a vaccine component as well as a reagent for identifying host antibodies raised against *Streptococcus pneumoniae* during infection. The purified protein can also be used in methods for detecting the presence of *Streptococcus pneumoniae*.

Unique fragments of the 37-kDa protein can be identified in the same manner as that used to identify unique nucleic acids. For example, a sequence of 3 amino acids or more, derived from the sequence of the 37-kDa protein as set forth in the Sequence Listing as SEQ ID NO:2 can be used to search the protein sequence databases. Those that do not match a known sequence are therefore unique.

"Purified protein" as used herein means the protein or fragment is sufficiently free of contaminants or cell components with which the protein normally occurs to distinguish the protein from the contaminants or cell components. It is not contemplated that "purified" necessitates having a preparation that is technically totally pure (homogeneous), but purified as used herein means the protein or polypeptide fragment is sufficiently separated from contaminants or cell components with which it normally occurs to provide the protein in a state where it can be used in an assay, such as immunoprecipitation or ELISA. For example, the "purified" protein can be in an electrophoretic gel.

Once a nucleic acid encoding a 37-kDa pneumococcal surface adhesin protein of serotype 6B, or a fragment of that nucleic acid, is constructed, modified, or isolated, that nucleic acid can then be cloned into an appropriate vector, which can direct the in vivo or in vitro synthesis of that 37-kDa pneumococcal surface adhesin protein, or fragment thereof The vector is contemplated to have the necessary functional elements that direct and regulate transcription of the inserted gene, or gene fragment. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or gene fragment. (See generally, Sambrook et al.).

There are numerous *E. coli* (*Escherichia coli*) expression vectors known to one of ordinary skill in the art which are useful for the expression of the nucleic acid insert. Other microbial hosts suitable for use include bacilli, such as *Bacillus subtilis*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, a promoter system from phage lambda, or other phage promoters such as T4 or T7 promoters. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures.

Alternatively, viral expression systems can be used to express the nucleic acid of the present invention, or fragments thereof For example, vaccinia virus vectors can accept large inserts and can be used to express foreign genes for vaccination purposes. (See, e.g., Fredman, T. Science 244:1275 (1989)). Other viral expression systems, such as the baculovirus expression system, are also commonly used in the art.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF"-1 gene) is routinely used to direct protein secretion from yeast. (Brake el al, "∝-Factor-Directed Synthesis and Secretion of Mature Foreign Proteins in *Saccharomyces cerevisiae*." Proc. Nat. Acad. Sci., 81:4642–4646 (1984)). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha-factor leader region. This construct is then put under the control of a strong transcription promoter, such as the alcohol dehydrogenase I promoter or a glycolytic promoter. The nucleic acid coding sequence is followed by a translation termination codon which is followed by transcription termination signals. Alternatively, the nucleic acid coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, addition of lipid moieties, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, gentamicin resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation, transduction, and electroporation are commonly utilized for prokaryotic cells, whereas calcium phosphate, DEAE dextran, or lipofectin mediated transfection or electroporation may be used for other cellular hosts.

Alternative vectors for the expression of genes in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acids in mammalian cells (such as COS-7).

Expression of the gene or hybrid gene can be by either in vivo or in vitro. In vivo synthesis comprises transforming prokaryotic or eukaryotic cells that can serve as host cells for the vector. Alternatively, expression of the gene can occur in an in vitro expression system. For example, in vitro transcription systems are commercially available which are routinely used to synthesize relatively large amounts of mRNA. In such in vitro transcription systems, the nucleic acid encoding the 37-kDa pneumococcal surface adhesin protein would be cloned into an expression vector adjacent to a transcription promoter. For example, the Bluescript II cloning and expression vectors contain multiple cloning sites which are flanked by strong prokaryotic transcription promoters. (Stratagene Cloning Systems, La Jolla, Calif.). Kits are available which contain all the necessary reagents for in vitro synthesis of an RNA from a DNA template such as the Bluescript vectors. (Stratagene Cloning Systems, La Jolla, Calif.). RNA produced in vitro by a system such as this can then be translated in vitro to produce the desired 37-kDa pneumococcal surface adhesin protein. (Stratagene Cloning Systems, La Jolla, Calif.).

Another method of producing a 37-kDa pneumococcal surface adhesin protein is to link two peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to a 37-kDa pneumococcal surface adhesin protein can be synthesized by standard chemical reactions, either continuous synthesis or step-wise synthesis. For example, a partial polypeptide can be synthesized and not cleaved from its synthesis resin whereas another fragment can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a 37-kDa pneumococcal surface adhesin protein. (Grant G. A., "Synthetic Peptides: A User Guide," W. H. Freeman and Co., N.Y. (1992) and Bodansky, M and Trost, B., Ed., "Principles of Peptide Synthesis," Springer-Verlag Inc., N.Y. (1993)). Alternatively, the 37-kDa pneumococcal surface adhesin protein can by independently synthesized in vivo as described above. Once isolated, these independent polypeptides may be linked to form a 37-kDa pneumococcal surface adhesin protein via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al., "Synthesis of Proteins by Native Chemical Ligation," *Science*, 266:776–779 (1994)). The first step is the chemoselective reaction of an unprotected synthetic peptide-α-thioester with another unprotected peptide segment containing an amino-tenninal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8)

(Clark-Lewis et al., FEBS Lett., 307:97 (1987), Clark-Lewis et al, J. Biol. Chem., 269:16075 (1994), Clark-Lewis et al., Biochem. 30:3128 (1991), and Rajarathnam et al., Biochem. 29:1689 (1994)).

Alternatively, unprotected peptide segments can be chemically linked where the bond formed between the peptide segments as a result of the chemical ligation is an unnatural (non-peptide) bond (Schnolzer et al., Science, 256:221 (1992)). This technique has been used to synthesize analogs of protein domains as well as large amounts of relatively pure proteins with full biological activity (deLisle Milton el al., "Techniques in Protein Chemistry IV," Academic Press, New York, pp. 257–267 (1992)).

The invention also provides fragments of the 37-kDa pneumococcal surface adhesin protein. The polypeptide fragments of the present invention can be recombinant proteins obtained by cloning nucleic acids encoding fragments of the polypeptide in an expression system capable of producing the polypeptide fragments thereof, as described above for the 37-kDa protein. For example, one can determine an immunoreactive region of a 37-kDa pneumococcal surface adhesin protein which can cause a significant immune response, clone the nucleic acid encoding that polypeptide into an expression vector, and isolate that particular polypeptide for further uses, such as diagnostics, therapy, and vaccination. In one example, amino acids found to not contribute to the immunoreactivity and/or specificity can be deleted without a loss in the respective activity.

For example, amino or carboxy-terminal amino acids, can be sequentially removed from the 37-kDa pneumococcal surface adhesin protein and the immunoreactivity tested in one of many available assays. Alternatively, internal amino acids can be sequentially removed and the immunoreactivity tested for each of the deletions. In another example, a fragment of a 37-kDa pneumococcal surface adhesin protein can comprise a modified polypeptide wherein at least one amino acid has been substituted for the naturally occurring amino acid at specific positions, or a portion of either amino terminal or carboxy terminal amino acids, or even an internal region of the polypeptide, can be replaced with a polypeptide fragment or other moiety, such as biotin, which can facilitate in the purification of the modified 37-kDa pneumococcal surface adhesin protein. For example, a modified 37-kDa pneumococcal surface adhesin protein can be fused to a maltose binding protein, through either peptide chemistry of cloning the respective nucleic acids encoding the two polypeptide fragments into an expression vector such that the expression of the coding region results in a hybrid polypeptide. The hybrid polypeptide can be affinity purified by passing it over an amylose affinity column, and the modified 37-kDa pneumococcal surface adhesin protein can then be separated from the maltose binding region by cleaving the hybrid polypeptide with the specific protease factor Xa. (See, e.g., New England Biolabs Product Catalog, 1996, pg. 164.)

Immnunoreactive fragments of a 37-kDa pneumococcal surface adhesin protein can also be synthesized directly or obtained by chemical or mechanical disruption of larger 37-kDa pneumococcal surface adhesin protein. An immunoreactive fragment is defined as an amino acid sequence of at least about 6 consecutive amino acids derived from the naturally occurring amino acid sequence, which has the relevant activity, e.g., evoking an immune response.

The fragments, whether attached to other sequences or not, can also include insertions, deletions, substitutions, or other selected modifications of particular regions or specific amino acids residues, provided the immunoreactivity of the peptide is not significantly impaired compared to the 37-kDa pneumococcal surface adhesin protein. These modifications can provide for some additional property, such as to remove/ add amino acids capable of disulfide bonding, to increase its bio-longevity, etc. In any case, the peptide must possess a bioactive property, such as immunoreactivity. Functional or active regions of the 37-kDa pneumococcal surface adhesin protein may be identified by mutagenesis of a specific region of the protein, followed by expression and testing of the expressed polypeptide. Such methods are readily apparent to a skilled practitioner in the art and can include site-specific mutagenesis of the nucleic acid encoding the receptor. (See, e.g., Smith, M. "In vitro mutagenesis" Ann. Rev. Gen., 19:423–462 (1985) and Zoller, M. J. "New molecular biology methods for protein engineering" Curr. Opin. Struct. Biol., 1:605–610 (1991)).

Antibodies

The present invention also provides a purified antibody which selectively binds with the polypeptide encoded by the nucleic acid set forth in the sequence listing as SEQ ID NO:1, or a polypeptide encoded by a unique fragment of at least 10 nucleotides of SEQ ID NO:1. The antibody (either polyclonal or monoclonal) can be raised to the 37-kDa pneumococcal surface adhesin protein of a unique fragment thereof, in its naturally occurring form and in its recombinant form. The antibody can be used in techniques or procedures such as diagnostics, treatment, or vaccination.

Antibodies can be made by many well-known methods (See, e.g. Harlow and Lane, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., *Bio/Technology*, 10:163–167 (1992); Bebbington et al., *Bio/Technology*, 10:169–175 (1992)).

The phrase "selectively binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, (1988)).

The present invention also provides a monoclonal antibody designated 1E7A3D7C2, or a fragment thereof which retains the characteristics of antibody 1E7A3D7C2, such as its binding specificity and its binding affinity.

The present invention also provides a monoclonal antibody designated 1B6E12H9, or a fragment thereof which retains the characteristics of antibody 1B6E12H9.

The present invention also provides a monoclonal antibody designated 3C4D5C7, or a fragment thereof which retains the characteristics of antibody 3C4D5C7.

The present invention also provides a monoclonal antibody designated 4E9G9D3, or a fragment thereof which retains the characteristics of antibody 4E9G9D3.

The present invention also provides a monoclonal antibody designated 4H5C10F3, or a fragment thereof which retains the characteristics of antibody 4H5C10F3.

The present invention also provides a monoclonal antibody designated 6F6F9C8, or a fragment thereof which retains the characteristics of antibody 6F6F9C8.

The present invention also provides a monoclonal antibody designated 8G12G11B10, or a fragment thereof which retains the characteristics of antibody 8G12G11B10.

Vaccines

Also provided by thy present invention is a vaccine comprising an immunogenic polypeptide encoded by the nucleic acid as set forth in the Sequence Listing as SEQ ID NO:1, or a unique fragment of at least 10 nucleotides of SEQ ID NO:1. The polypeptides provided by the present invention can be used to vaccinate a subject for protection from a particular disease, infection, or condition caused by the organism from which the 37-kDa pneumococcal surface adhesin protein of a unique fragment thereof was derived.

Polypeptides of a 37-kDa pneumococcal surface adhesin protein of serotype 6B or a unique fragment thereof therefore, can be used to inoculate a host organism such that the host generates an active immune response to the presence of the polypeptide or polypeptide fragment which can later protect the host from infection by organism from which the polypeptide was derived. One skilled in the art will appreciate that an immune response, especially a cell-mediated immune response, to a 37-kDa pneumococcal surface adhesin protein from a specific strain can provide later protection from reinfection or from infection from a closely related strain. The 37-kDa protein provided by the present invention, however, is relatively conserved among many of the various serotypes of *S. pneumoniae* and can serve as a multivalent vaccine.

Immunization with the 37-kDa pneumococcal surface adhesin protein can be achieved through artificial vaccination. (Kuby, J. "Immunology" W. H. Freeman and Co. New York, 1992). This immunization may be achieved by administering to subjects the 37-kDa pneumococcal surface adhesin protein either alone or with a pharmaceutically acceptable carrier.

Immunogenic amounts of the 37-kDa pneumococcal surface adhesin protein can be determined using standard procedures. Briefly, various concentrations of the present polypeptide are prepared, administered to subjects, and the immunogenic response (e.g., the production of antibodies to the polypeptide or cell mediated immunity) to each concentration is determined. Techniques for monitoring the immunogenic response, both cellular and humoral, of patients after inoculation with the polypeptide, are very well known in the art. For example, samples can be assayed using enzyme-linked immunosorbent assays (ELISA) to detect the presence of specific antibodies, such as serum IgA (Hjelt et al. J. Med. Virol. 21:39–47, (1987)), or lymphocyte or cytokine production can be monitored. The specificity of a putative immunogenic antigen of any particular polypeptide can be ascertained by testing sera, other fluids or lymphocytes from the inoculated patient for cross-reactivity with other closely related 37-kDa pneumococcal surface adhesin proteins.

The amount of a polypeptide of the 37-kDa pneumococcal surface adhesin protein administered will depend on the subject, the condition of the subject, the size of the subject, etc., but will be at least an immunogenic amount. The polypeptide can be formulated with adjuvants and with additional compounds, including cytokines, with a pharmaceutically acceptable carrier.

It is also contemplated that immunization against *Streptococcus pneumoniae* can be achieved by a "naked" DNA vaccine approach. Briefly, DNA constructs containing promoter sequences upstream of the 37-kDa protein or specific antigen coding sequences can be injected into muscle tissue or administered via the mucosa and result in expression of viral antigens that induce a protective immune response.

The pharmaceutically acceptable carrier or adjuvant in the vaccine of the present invention can be selected by standard criteria (Arnon, R (Ed.) "Synthetic Vaccines" I:83–92, CRC Press, Inc. Boca Raton, Fla., 1987). By "pharmaceutically acceptable" is meant a material that is not biologically or otherwise undesirable, i.e., the material may be administered to an individual along with the selected compound without causing any undesirable biological effects or interacting in a undesirable manner with any of the other components of the pharmaceutical composition in which it is contained. The carrier or adjuvant may depend on the method of administration and the particular patient.

Methods of administration can be by oral, sublingual mucosal, inhaled, absorbed, or by injection. Actual methods of preparing the appropriate dosage forms are known, or will be apparent, to those skilled in this art; for example, see Remington's Pharmaceutical Sciences (Martin, E. W. (ed.) latest edition Mack Publishing Co., Easton, Pa.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Detection Methods

The present invention also provides a method of detecting the presence of the *Streptococcus pneumoniae* in a sample, comprising the steps of contacting a sample suspected of containing *Streptococcus pneumoniae* with nucleic acid primers capable of hybridizing to a nucleic acid comprising a unique portion of the nucleic acid set forth in the Sequencing Listing as SEQ ID NO:1, amplifying the nucleic acid, detecting the presence of an amplification product, the presence of the amplification product indicating the presence of *Streptococcus pneumoniae* in the sample. Alternatively, a unique fragment of the nucleic acid of SEQ ID NO:1 can be used to specifically identify a non-selectively amplified nucleic acid.

The specific amplification methods are well known in the art. For example, and as disclosed in the Example contained herein the polymerase chain reaction (PCR) can be used to amplify nucleic acid in a sample specific for *Streptococcus pneumoniae*. Other amplification techniques can also be used to detect the presence of *Streptococcus pneumoniae* in a sample, such as the ligase chain reaction (LCR), the self-sustained sequence replication (3SR) system, the transcription-based amplification system (TAS), and the RNA replication system based on Qβ replicase.

The amplified nucleic acid can be detected in any number of detection assays. For example, the primers can be radiolabeled such that the amplification product containing these primers can be detected by the detecting the radioactive decay from those primers. Alternatively, the primers can contain other detectable moieties, such as biotin, or the amplified nucleic acid can be stained and visualized, such as with ethidium bromide staining.

The present invention also provides a method of detecting the presence of *Streptococcus pneumoniae* in a subject, comprising the steps of contacting an antibody-containing sample from the subject with purified polypeptide encoded by the nucleic acid set forth in the Sequence Listing as SEQ ID NO:1, or a purified polypeptide encoded by a nucleic acid comprising a unique fragment of at least 10 nucleotides of SEQ ID NO:1, and detecting the binding of the antibody with the polypeptide, the binding indicating the presence of *Streptococcus pneumoniae* in the subject.

The present invention further provides a method of detecting the presence of *Streptococcus pneumoniae* in a subject, comprising the steps of contacting a sample from the subject with an antibody which selectively binds the purified polypeptide encoded by the nucleic acid set forth in the Sequence Listing as SEQ ID NO:1, or a purified polypeptide encoded by a nucleic acid comprising a unique fragment of at least 10 nucleotides of SEQ ID NO:1 and detecting the binding of the antibody with an antigen, the binding indicating the presence of *Streptococcus pneumoniae* in the subject.

There are numerous immunodiagnostic methods that can be used to detect antigen or antibody as the following non-inclusive examples illustrate. These methods, as well as others, can not only detect the presence of antigen or antibody, but quantitate antigen or antibody as well.

Immunoassays such as immunofluorescence assays (IFA), enzyme linked immunosorbent assays (ELISA) and immunoblotting can be readily adapted to accomplish the detection and quantitation of the antigen or antibody. An ELISA method effective for the detection of the antigen, for example, can be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.

Another immunologic technique that can be useful in the detection utilizes monoclonal antibodies (MAbs) for detection of antibodies that specifically bind a specific antigen. Briefly, sera or other body fluid from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition can be a specific test for a particular species or subspecies or variety or strain since it is based on monoclonal antibody binding specificity. MAbs can also be used for detection directly in cells by IFA.

A micro-agglutination test can also be used to detect the presence of antibodies in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or detectable by a spectrophotometer. In a modification of the above test, antibodies specifically reactive with the antigen can be bound to the beads and antigen in the tissue or body fluid thereby detected.

In addition, as in a typical sandwich assay, the antibody can be bound to a substrate and contacted with the antigen. Thereafter, a labeled secondary antibody is bound to epitopes not recognized by the first antibody and the secondary antibody is detected.

In the diagnostic methods taught herein, the antigen can be bound to a substrate and contacted by a fluid sample such as serum, urine, saliva or gastric juice. This sample can be taken directly from the subject, or in a partially purified form. In this manner, antibodies specific for the antigen (the primary antibody) will specifically bind with the bound antigen. Thereafter, a secondary antibody bound to, or labeled with, a detectable moiety can be added to enhance the detection of the primary antibody. Generally, the secondary antibody or other ligand which binds specifically with a different epitope of the antigen or nonspecifically with the ligand or bound antibody, will be selected for its ability to bind with multiple sites on the primary antibody. Thus, for example, several molecules of the secondary antibody can bind with each primary antibody, making the primary antibody more detectable.

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow et al., "Antibodies: A Laboratory Manual" Cold Spring Harbor Laboratory, Cold Spring Harbor, N.Y., (1988)).

Methods of Treating and Preventing Infection

The present invention also provides a method of preventing *Streptococcus pneumoniae* infection in a subject, comprising administering to the subject a prophylactically effective amount of a vaccine comprising an immunogenic polypeptide encoded by the nucleic acid encoding the 37-kDa protein of *Streptococcus pneumoniae* as set forth in the Sequence Listing as SEQ I) NO:1, or an immunogenic polypeptide encoded by a nucleic acid comprising a unique fragment of at least 10 nucleotides of SEQ ID NO:1, either alone or with a pharmaceutically acceptable carrier.

The present invention further provides a method of preventing *Streptococcus pneumoniae* infection in a subject, comprising administering to the subject a prophylactically effective amount of an anti-idiotype antibody to the polypeptide encoded by the nucleic acid as set forth in the Sequence Listing as SEQ ID NO:1, or a polypeptide encoded by a nucleic acid comprising a unique fragment of at least 10 nucleotides of SEQ ID NO:1, either alone or with a pharmaceutically acceptable carrier.

Anti-idiotype antibodies represent the image of the original antigen and can serve as a vaccine to induce an immune response to a pathogenic antigen, therefore avoiding immunization with the pathogen itself This type of protection has been demonstrated by immunizing mice with anti-idiotype antibody to the binding site of TEPC-15, the major component of the pneumococcal cell wall C polysaccharide. Mice immunized with these anti-idiotype antibodies were immune when they were later challenged with live pneumococci. Mice have also been used to demonstrate anti-idiotype antibodies can provide protection against hepatitis B virus, rabies virus, Sendai virus, *Streptococcus pneumoniae, Listeria monocytogenes, Trypanosoma rhodesiense*, and *Schistosoma mansoni*. (See, Kuby, J. "Immunology" W. H. Freeman and Co. New York, 1992).

The present invention further provides a method of treating a *Streptococcus pneumoniae* infection in a subject, comprising administering to the subject a therapeutically effective amount of an antibody to the polypeptide encoded by the nucleic acid as set forth in the Sequence Listing as SEQ ID NO:1, or a polypeptide encoded by a nucleic acid comprising a unique fragment of at least 10 nucleotides of SEQ ID NO:1, either alone or with a pharmaceutically acceptable carrier.

Treating a subject already infected with a particular organism by administering to the subject antibody against the organism is well known in the art. For example, immune globulin isolated from animals or humans previously exposed to rabies virus is currently a therapy for rabies virus infection. Better treatment of infected individuals can be achieved by administering to those individuals monoclonal antibodies since those monoclonals react or bind more specifically that the polyclonals. (See, e.g. Kaplan et at. "Rabies" Sci. Am. 242:120–134 (1980)).

The following example is put forth so as to provide those of ordinary skill in the art with a complete disclosure and description of how the attenuated prokaryotes claimed herein are made and evaluated, and demonstrates the methods of the present invention, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLES

Bacterial Strains

The *S. pneumoniae* strain R36A was kindly provided by D. E. Briles (University of Alabama at Birmingham). Twenty-four serotypes of *S. pneumoniae* were provided by R. Facklam, Centers for Disease Control (CDC), Atlanta, Ga. These serotypes are 1, 2, 3, 4, 5, 6A, 6B, 7F, 8, 9N, 9V, IOA, 11F, 11A, 12F, 14, 15B, 18C, 19A, 19F; 20, 22F, 23F, and 33F. Entex, ococcus avium, *E. casseliflavus*, and *E. gallinarum* were also provided by R. Facklam. Anaerobic bacteria were obtained from V. R. Dowell, CDC. These included *Bacteroides asaccharolyticus, B. fragilis, B. intermedivs, B. thetaiotaomicron, Eubacterium lentum, Fusobacterium necrophorum, F. nucleatum, Peptostreptococcus anaerobius, P. asaccharolyticus, Propionibacterium acnes*, and *Staphylococcus saccharolyticus*. *Branhamella catarrhalis* and *Bordetella parapertussis* were obtained from R. Weaver, CDC. *Mycobacterium tuberculosis* was provided by R. C. Good, CDC. R. Barnes, CDC, provided *Chlamydia pneumoniae*. The following remainig bacteria were from the stock collection of the Immunology Laboratory, CDC: *Bordetella pertussis, Enterobacter aerogenes, E. agglomerans, E. cloacae, E. gergoviae, Escherichia coli, Klebsiella pneumoniae, Haemophilus influenzae* (types a-f), *Legionella micdadei, L. pneumophila, Mycoplasma pneumoniae, Pseudomonas aeruginosa, Serratia marcescens, Staphylococcus aureus, Streptococcus agalactiae, S. equisimilis, S. pyogenes*, and group *G streptococci*.

Production of MAbs

Female BALB/c mice were immunized with whole cell suspensions of *S. pneumoniae* R36A, a rough derivative of the capsular type 2 strain D39 (Avery et al. (1944) J. Exp. Med. 79:13 7–157). The mice were immunized by intravenous injection three times and intraperitoneal injection one time. The maximum number of cells injected at any time was $10^8$. Fusion was done on day 25 by using standard procedures (Clafin et al. (1978) Curr. Top. Microbiol. Immunol. 81:107–109). Spleen cells of 4 mice were fused with Sp2/0-Ag14 myeloma cells (Schulman et al. (1978) Nature (London) 276:269–270). Culture fluids of the growing hybridomas were tested for antibodies to *S. pneumoniae* whole cells in an ELISA. A clone designated 1E7A3D7C2 was one of 10 selected for further study.

ELISA

Screening of hybridoma culture supernatants was done by ELISA. U-bottom microtitration plates (Costar, Cambridge, Mass.) were sensitized with 50 μl of *S. pneumoniae* whole cell suspension ($10^9$ CFU/ml) diluted 1:4,000 in 0.1 M carbonate buffer, pH 9.6, and kept for 16 h at 4° C. The plates were washed 5 times with 0.9% NaCl containing 0.05% Tween 20 NaCl—T). Culture supernatants (50 μl) from the fusion plates were added to 50 μl of a solution containing 2% bovine serum albumin (BSA), 10% normal rabbit serum, 0.3% Tween-20, and 0.02% Merthiolate in phosphate buffered saline (PBS), pH 7.2, (ELISA diluent) (Wells. et al. (1987) J. Clin. Microbiol. 25:516–521) in the plates and were incubated for 30 min at 37° C. The plates were washed 5 times with NaCl—T. Fifty microliters of goat anti-mouse immunoglobulin horseradish peroxidase conjugate, diluted in ELISA diluent was added to each well. The plates were incubated for 30 min at 370C. The plates were washed, and 50 μl of 3,3',5,5'-tetramethylbenzidine (0.1 mg/mi in 0.1M sodium acetate, 0.1 M citric acid (pH 5.7] with 0.005% hydrogen peroxide) was added to each well and incubated for 30 min at 37° C. The reaction was stopped by adding 1 ml of 4 M $H_2SO_4$ and the optical density was read on a Dynatech ELISA Reader (Dynatech Laboratories, Inc., Alexandria, Va.) at 450 nm. An optical density of >0.200 was considered positive.

SDS-PAGE and Immunoblot Analysis

Sodium dodecyl sulfate-polyacrylamide gel electrophoresis (SDS-PAGE) was performed by the method of Tsang et al. (Tsang et al. (1983) Methods Enzymol. 92:377–391), using an 8% acrylamide resolving gel. Equal volumes of sample buffer (5% SDS-10% 2-mercaptoethanol-20% glycerol in 0.01 M Tris HCL, [pH 8.0]) and cell suspension containing 2.4 μg protein per μl were mixed, heated at 100° C. for 5 min, and a 5-μl portion was applied to 1 of 15 wells. If the final protein content of the portion of sample to be tested was <1.2 μg/μl, a volume up to 10 μl of sample was applied to achieve a final concentration of 6 μl of protein per well. Protein concentrations were determined by the method of Markwell et al. (Markwell et al. (1978) Anal. Biochem. 87:206–210), with BSA as the standard.

Proteins separated by SDS-PAGE were either silver stained by the method of Morrissey (Momssey, J. H. (1981) Anal. Biochem. 117:307–310) or electroblotted onto nitrocellulose (Schleicher & Schnell, Inc., Keene, N. H.). The immunoblot procedure was done according to the method of Tsang et al. (Tsang et al. (1983) Methods Enzymol. 92:377–391) with slight modifications. The blots were given three 5-min washes with PBS, pH 7.2, containing 0.3% Tween-20 and were gently agitated overnight (16 h) at 25° C. The blots were blocked for 1 h with casein-thimerosal buffer (CTB) (Kenna et al. (1985) J. Immunol. Meth. 85:409419). After three rinses with CTB, the blots were exposed to goat anti-mouse immunoglobulin horseradish peroxidase conjugate (Bio-Rad Laboratories, Richmond, Calif.) for 2 h at 25° C. Conjugate dilutions (1:2,000) were made in CTB. The blots were again rinsed three times with CTB and exposed to 3-3' diaminobenzadine-4-hydrochloride in PBS, pH 7.2 (0.5mg/ml), with 0.003% $H_2O_2$ for 5 min at 25° C. Reactivity was expressed as a visible colored band on the nitrocellulose paper. Low molecular-mass protein standards (Bio-Rad) were used in PAGE and immunoblotting. Rabbit antisera to the protein standards were used to develop the standards (Carlone, G. M. (1986) Anal. Biochem. 155:89–91). Molecular masses were calculated by the method of Neville and Glossman (Neville et al. (1974) Methods Enzymol. 32:92–102) using appropriate molecular mass standards.

IFA

A bacterial suspension containing approximately 400–500 CFU per field (10 μl) was allowed to dry at room temperature on each well of acetone-resistant, 12-well (5 mm diameter), glass slides (25×75 mm) (Cel-Line Associates, Newfield, N.J.). The slides were then immersed in acetone for 10 min and air dried at room temperature. MAbs were added to the slides, which were incubated for 30 min at 37° C. After incubation, the slides were gently rinsed with PBS and soaked twice at 5-min intervals, blotted on filter paper, and air dried at room temperature. Fluorescein-labeled rabbit anti-mouse immunoglobulin (courtesy of W. F. Bibb, CDC) was then added, and the slides were incubated for 30 min at 37° C. They were then washed twice with PBS and gently blotted on filter paper. Slides were covered with carbonate-buffered mounting fluid, pH 9.0, and cover slips and were then read with a Leitz Dialux 20 fluorescence microscope equipped with a HBO-100 mercury incident light source, an I cube filter system, a 40x dry objective lens, and 6.3x binoculars (E. Leitz, Inc., Rockleigh, N.J.).

Immunoelectron-microscopy

Pneumococcal cells were washed two times with PBS and fixed in a mixture of 1% paraformaldehyde-0.1% glutaraldehyde (freshly made) for 20 min at 4° C. The cells were dehydrated in a graded alcohol series and then in a 1:1 mixture of absolute ethanol and Lowicryl K4M (Ladd Research Industries, Inc., Burlington, Vt.) for 1 h at 4° C. The cells were pelleted and suspended in a 1:2 mixture of absolute ethanol and Lowicryl K4M for 1 h at 4° C. They were again pelleted and suspended in Lowicryl K4M (undiluted) for 16 h at 4° C.

The cells were transferred to fresh Lowicryl K4M two times during the next 24-hour period. The Lowicryl K4M-treated cells were imbedded in gelatin capsules, which were placed inside a box lined with aluminum foil. The capsules were hardened by holding them in the box 35 cm from a short-wave UV light source for 72 h at −20° C. The box was brought to room temperature, and the capsules were allowed to continue hardening for up to 14 days.

Samples of the capsule were cut into 100-μm thin sections and picked up on nickel grids. Grids containing the sample were placed on a droplet of ovalbumin solution in PBS containing sodium azide (E. Y. Laboratories, Inc., San Mateo, Calif.) for 5 min. The grids (wet) were transferred to a solution of primary MAbs diluted in a solution of BSA reagent (1% BSA in PBS containing 0.1% Triton X-100, Tween 20, and sodium azide) (E. Y. Laboratories) and incubated for 1 h at room temperature or 18 to 48 h at 4° C. in a moist chamber. For antibody binding controls, other grids were wetted with MAbs against *Legionella pneumophila*. The grids were rinsed two times with PBS and incubated on droplets of goat anti-mouse IgG-labeled colloidal gold particles (20 μm)(E. Y. Laboratories) for 1 h at room temperature. The grids were rinsed two times and post-stained with osmium tetroxide, uranyl acetate, and lead citrate. The grids were examined with a Philips 410 transmission electron microscope.

CBA/CaHN/J Mice

X-linked immune deficiency (xid) of CBA/N mice as prepared by Wicker, L. S. and I. Seher, Curr. Top. Microbiol. Immunol. 124:86–101 were used to study the protection afforded by the 37 kDa protein.

Example 1

Monoclonal Antibodies

Hybridoma clone 1E7A3D7C2 produced MAbs that reacted with a 37-kilodalton (kDa) protein antigen (pneumococcal fimbrial protein A) found in *S. pneumoniae*. The MAbs reacted with an antigen fractionated in SDS-PAGE, yielding a single immunoblot band. This indicates that the MAb reacted with epitopes found only on the 37-kDa antigen (pneumococcal fimbrial protein A). The MAbs produced by the immunization of mice with pneumococcal cells reacted with all pneumococcal strains tested (24 serotypes) to yield a sensitivity of 100%. For specificity, 55 different nonpneumococcal strains of bacteria that can also cause respiratory infections (Donowitz et al. (1985) In: Principles and practices in infectious diseases, 2nd ed. (G. L. Mandell, R. G. Douglas, and J. E. Bennett, ed.) John Wiley & Sons, Inc., New York, pp.394–404) were tested for antigens reacting with the MAbs. The latter strains represented 19 genera and 36 species of bacteria. None of the strains tested reacted with the pneumococcal MAbs, thus yielding a specificity of 100%.

Of 44 patients known to have pneumococcus disease, 34 (77%) had antibodies that reacted with the 37-kDa antigen (pneumococcal fimbrial protein A) by Western immunoblot.

The MAbs reacted with whole pneumococcal cells to yield a positive test result in both the ELISA and IFA. Results from both the ELISA and the IFA indicate that the antigen has exposed epitopes on the surface of the cell or that the immunoglobulin and other immunologic reagents are able to penetrate the pneumococcal cell walls.

Several strains of group A streptococci were tested for imnimunofluorescence after reacting with the pneumococcus MAbs. None of the heterologous bacterial cells fluoresced in this test, indicating that the IFA reaction was specific for pneumococcus cells.

To further determine the location on the cell of the 37-kDa antigen (pneumococcal fimbrial protein A) epitopes reacting with the MAbs, immunolabeling experiments were performed. The cells were typical of gram-positive cocci in the process of division. A large portion of the antigen appears to be intracellular since there is no coating or layering of the labeled MAbs around the cell. The large patch of colloidal gold staining indicates that the MAbs bound antigen located inside the cell wall. There was no colloidal gold binding to control pneumococci that were exposed to the MAbs against *L. pneumophila*.

Example 2

Cloning of the Pneumococcal Fimbrial Protein A Gene

*Streptococcus pneumoniae* DNA digested with restriction enzyme Sau3Al was ligated to BamHI digested pUC13 and transformed into *E. coli* TB1. Recombinant clones were identified by colony immunoblot using the 37-kDa monoclonal antibody. The plasmid pSTR3-1 is an example of the pneumococcal-fimbrial protein A gene cloned into pUC13.

Example 3
Preparation of Purified 37 kDa Protein Antigen

Two methods for preparing the 37 kDa protein are used. (1) *Streptococcus pneumoniae* is conventionally cultured and the cells harvested. Purified 37 kDa protein antigen (pneumococcal fimbrial protein A) is isolated from the *Streptococcus pneumoniae* cell mass by extraction with a non-ionic detergent and further purified by ammonium sulfate fractionation and isoelectric focusing. (2) *E. coli* TB1 strains containing plasmid pSTR3-1 is cultured conventionally and the cells harvested. For improved yields, *E. coli* strains, transformed with an expression vector that carries a strong, regulated prokaryotic promoter and which contains the gene coding for the 37 kDa protein, is used. Suitable expression vectors are those that contain a bacteriophage λPL Promoter (e.g., pKK1773-3), a hybrid trp-lac promoter (e.g., pET-3a) or a bacteriophage T7 promoter. The 37 kDa protein (PfpA) is then extracted from the separated cell mass.

Protection Experiments with 37 kDa Protein
Experiment No. 1

Twenty CBA/CaHN/J mice carrying the xid (x-linked immunodeficiency) mutation were used in this protection study. They were tested for protection against challenge with a virulent type 3 *Streptococcus pneumoniae* strain, WU2. Mice were anesthetized with Ketamine/Rompun and bled infraorbitally to obtain pre-immunization sera. 37-kDa protein (pneumococcal fimbrial protein A) was emulsified in complete Freund's adjuvant (CFA) to a protein concentration of 54 µg per ml. Ten mice were injected subcutaneously into 2 axillary and 2 inguinal sites at 0.1 ml per site, delivering approximately 22 µg protein/mouse. Ten control mice were treated identically with CFA and buffer substituting for protein. Fourteen days later, the ten test mice were injected intraperitoneally (IP) with 100 µg of the 37-kDa protein; controls were injected IP with buffer eight days following the IP immunizations, all mice were bled infraorbitally to obtain post-immunization sera, and challenged intravenously (IV) with 60 CFU of a log phase culture of *S. pneumoniae* strain WU2, a virulent capsular type 3 strain. Mice were observed for 21 days, and deaths were recorded.

Sera were collected prior to immunizations to establish baseline exposures, and also following the full immunization protocol (but before challenge) in order to correlate circulating antibody to the 37 kDa protein with protection.

Days post challenge: 1—no deaths
 2—3 control mice dead
 3—2 control mice dead
 4—2 control mice dead, one sick
 5—1 control mouse dead
 6—21 no deaths
Immunized with 37 kDa protein: 10/10 survived
Controls with no protein: 2/10 survived (8/10 died)
Difference statistically significant: (p=0.0008) Rank sum test Experiment No. 2

Twenty CBA/CaHN/J mice carrying the xid mutation were injected according to the following protocol:

1. All mice were bled prior to immunization to establish baseline immunity. Ten test mice were immunized subcutaneously in four sites with a total of 21 µg of 37-kDa protein antigen (pneumococcal fimbrial protein A) emulsified in Complete Freund's adjuvant (CFA). Ten control mice were immunized identically with CFA and buffer substituting for the antigen.

2. Fourteen days later, the mice were boosted intraperitoneally (I.P.) with 100 µg of the 37 kDa protein antigen (test mice) or with buffer (controls). No adjuvant was used with this booster immunization.

3. Eight days later, all mice were bled via the infraorbital sinus and the sera were collected and pooled into the two groups (immunized and controls). At the same time, blood was collected from individual mice to assay for antibody responses.

4. One day later, two additional mice were injected I.O. with 0.1 ml of pooled immune sera to attempt to passively transfer immunity. Three additional mice were injected I.P. with 0.1 ml of pooled control mouse sera. (only five mice were injected at this step because of the small amount of sera obtained from the immunized mice.).

5. One hour after the I.P. injections, these five mice were challenged intravenously (I.V.) with 140 colony-forming units (CFU) of a mid-log phase pneumococcal type 3 strain, WU2.

6. At the same time, the eighteen (8 test and 10 control)* mice were challenged I.V. with the same culture of WU2.

7. Deaths were tallied daily.

| RESULTS: | No. Dead/No. Challenged |
|---|---|
| Immunized with the 37 kDa protein: | 0/8* |
| Control mice: | 10/10 |
| Passive Protection: | |
| mice receiving immune sera: | 0/2 |
| Mice receiving control sera: | 3/3 |

*Two of ten test mice died of other causes prior to challenged with WU2.

Mice immunized with the 37 kDa protein were protected from fatal challenge with strain WU2, and this immunity could be passively transferred with sera from immunized mice.

Experiment No. 3

An enzymne-linked immunosorb6nt assay (ELISA) was developed using purified *S. pneumoniae* 37-kDa protein antigen as a capture for human antibodies. Paired sera were tested from children, less than 24 months of age, known to have pneumococcal pneumonia. Disease confirmation was determined by blood culture or antigen in the urine. It was found that 35% (9/26) had antibody titers greater than sera from non-ill children of the same age group, p=0.06. This illustrates that some of the children responded to the 37-kDa protein antigen after natural infection.

Preparation of the 37 kDa Protein or Polypeptide Conjugate

Conjugates can be prepared by use of a carrier protein bound to the 37-kDa protein or polypeptides derived from the 37-kDa protein via a linker, to elicit a T cell dependent response. Such carrier proteins could be any immunogenic protein, for example, keyhole limpet hemocyanin, bovine serum albumin, tetanous toxoid, diphtheria toxoid, and bacterial outer membrane proteins. Examples of bacterial outer membrane proteins, useful as conjugates, include outer membrane proteins of *Neisseria meningitides* and *Haemophilus influenzae*. *Neisseria meningitides* can be an organism selected from *Neisseria meningitides*, group A, B, or C.

In addition, the 3 7-kDa protein or polypeptides thereof can be used in a conjugate where the 37-kDa protein or polypeptides thereof are the T-cell dependent immunogenic carrier for polysaccharide antigens that are B-cell stimulators. This is based on the theory that polysaccharide antigens are B-cell stimulators and that protective immunity is usually generated by a combination of B-cell and T-cell stimulation. Protein antigens exhibit T-cell dependent properties; i.e., booster and carrier priming. T-cell dependent stimulation is important because children less than two years of age do not respond to T-cell independent antigens. The attachment or conjugation of antigens can be accomplished by conventional processes, such as those described in U.S. Pat. No. 4,808,700, involving the addition of chemicals that enable the formation of covalent chemical bonds between the carrier immunogen and the immunogen.

In use, the 37-kDa protein antigen of this invention can be administered to mammals; e.g., human, in a variety of ways. Exemplary methods include parenteral (subcutaneous) administration given with a nontoxic adjuvant, such as an alum precipitate or peroral administration given after reduction or ablation of gastric activity; or in a pharmaceutical form that protects the antigen against inactivation by gastric juice (e.g., a protective capsule or microsphere).

The dose and dosage regimen will depend mainly upon whether the antigen is being administered for therapeutic or prophylactic purposes, the patient, and the patient's history. The total pharmaceutically effective amount of antigen administered per dose will typically be in the range of about 2 μg to 50 μg per patient.

For parenteral administration, the antigen will generally be formulated in a unit dosage injectable form (solution, suspension, emulsion) in association with a pharmaceutically acceptable parenteral vehicle. Such vehicles are inherently nontoxic and nontherapeutic. Examples of such vehicles include water, saline, Ringer's solution, dextrose solution, and 5% human serum albumin. Non aqueous vehicles, such as fixed oils and ethyl oleate, may also be used. Liposomes may be used as vehicles. The vehicle may contain minor amounts of additives, such as substances which enhance isotonicity and chemical stability; e.g., buffers and preservatives.

Example 4

Bacterial Strains.

All isolates of *S. pneumoniae* were provided and serotyped by the Streptococcal Reference Laboratory, Division of Bacterial and Mycotic Diseases, NCID, Centers for Disease Control and Prevention (CDC). The pneumococcal serotype 6B strain used for cloning and sequencing was a CDC reference strain (SP-86). *E. coli* DH5 α (Bethesda Research Laboratories, Gaithersburg, Md.) was used as the recipient host for plasmids, pUC19 and its derivatives.

*S. pneumoniae* strains were grown on Trypticase soy agar plates with 5% sheep blood cells or, where indicated, in Todd-Hewitt broth containing 0.5% yeast extract. *E. coli* cultures were grown in Luria broth which, when required, was supplemented with 100 μg/ml of ampicillin (Sigma Chemical Co., St. Louis, Mo.).

Cloning and Sequencing of the PsaA Gene from *S. pneumoniae*, Serotype 6b.

A chromosomal library from *S. pneumoniae* serotype 6B was prepared as previously described (Sampson et al. 1994. Cloning and nucleotide sequence analysis of psaA, the *Streptococcus pneumoniae* gene encoding a 37-ilodalton protein homologous to previously reported Streptococcus sp. adhesins. Infect. Immun. 62:319–324.), except that pUC18 was used as the cloning vector instead of pUC 13. Recombinants were screened by colony immunoblot using monoclonal antibody (MAb) 1E7. (Russell et al. 1990. Monoclonal antibody recognizing a species-specific protein from *Streptococcus pneumoniae*. J. Clin. Microbiol. 28:2191–2195). This procedure, as well as plasmid purification from positive clones (Ish-Horowicz et al. 1981. Rapid and efficient cosmid cloning. Nucleic Acids Res. 9:2989–2998.) and restriction endonuclease analysis, has all been previously described. (Sampson et al. 1990. Nucleotide sequence of htpB, the *Legionella pneumophila* gene encoding the 58-kilodalton (kDa) common antigen, formerly designated the 60-kDa common antigen. Infect. Immun. 58:3154–3157 and Sampson et al. 1994). Sodium dodecyl sulfate-polyacrylamide gel electrophoresis (SDS-PAGE) and Western blot analysis were done as before (Sampson et al. 1990). All other DNA manipulations were done according to methods described in Sambrook et al. DNA sequencing was performed using the ABI PRISM Dye Terminator Cycle Sequencing kit and procedure (Perkin-Elmer, Cetus, Foster City, Calif.). Sequence data were analyzed with the DNASTAR software program (DNASTAR Inc., Madison, Wis.) and the Wisconsin Genetics Computer Group sequence analysis software program (Fenno et al 1989. Nucleotide sequence analysis of a type 1 fimbrial gene of *Streptococcus sanguis* FW213. Infect. Immun. 57:3527–3533).

Preparation of Genomic DNA for PCR-RFLP Analysis.

High molecular weight pneumococcal DNA was prepared by the procedure of Graves and Swaminathan (Graves el al. 1993. Universal bacterial DNA isolation procedure, p. 617–621. In D. H. Pershing et al. (ed), Diagnostic molecular biology. American Society for Microbology, Washington, D.C.) with modifications. Sixteen-hour cultures of type specific *S. pneumoniae* were grown in 50 ml of Todd-Hewitt broth containing 0.5% yeast extract in screw cap flasks at 37° C. without shaking. Cultures were pelleted at 8000×g for 15 min at room temperature and washed with phosphate-buffered saline (10 mM, pH 7.2). The cell pellet was solubilized in 2.5 ml of buffer composed of 10 mM Tris, 1.0 mM EDTA, pH 8.0, and 0.4% SDS. Fifteen microliters of proteinase K (20 mg/ml) was added, and the lysate was incubated at 37° C. for 1 h. The mixture was adjusted to 0.48 M NaCl with the addition of 500 μl of 5M NaCl and, after mixing by inversion, 400 μl of 10% hexadecyltrimethylanmonium bromide in 0.7% NaCl was added. This suspension was mixed as before, incubated for 30 min at 65° C., and extracted with an equal volume of phenol-chloroform-isoamyl alcohol. The upper aqueous phase was separated by centrifugation at 1500×g and extracted with chloroform-isoarnyl alcohol. DNA was precipitated from the upper aqueous phase with 2.5 volumes of ethanol at −70° C. for 30 min. It was pelleted and dried in a desiccator, resuspended in water and quantitated by measuring absorbance at 260 nm.

PCR-RFLP.

Restriction enzymes EcoRI, HinfI, MaeIII, MboII, MnlI, and NheI were obtained from Boerhringer Mannheim Biochemicals (Indianapolis, Ind.); RsaI, Tsp509I, Eco57I, and XmnI were purchased from New England Biolabs (Beverly, Mass.). Primer sequences for the amplification reaction were selected from the N-terminal (nucleotides 181–201) and C-terminal (nucleotides 1106–1126) sequences of the *S. pneumoniae* serotype 6B gene (P1, AGGATCTAAT-GAAAAAATTAG (SEQ ID NO:3); P2, TCAGAGGCT-TATTTTGCCAAT (SEQ ID NO:4)) and flanking regions. The primers were synthesized at the Centers for Disease Control and Prevention using standard procedures.

(i) DNA amplification. The reaction was performed with the Perkin-Elmer PCR amplification kit. Reaction volumes were 100 μl and contained the standard 1× reaction buffer without Mg, 1 μM of each primer, 2.0 mM MgCl$_2$, 0.2 mM dNTPs, template DNA, and 2.5 U of Taq DNA polymerase. The source of the template DNA was either extracted purified chromosomal DNA or a bacterial colony. Conditions for amplification were as follows: 30 cycles of denaturation 94° C., 1 min., annealing 52° C., 0.5 min., and extension 72° C., 1.5 min. Amplified products were separated on a 1% agarose gel and visualized with ethidium bromide. A direct colony amplification procedure was adapted, which shortened template preparation by eliminating the necessity of extracting chromosomal DNA. The procedure consisted of adding a single bacterial colony directly from the plate into the PCR reaction mixture and heating at 95° C. for 10 minutes. The remaining PCR steps were performed as outlined for extracted chromosomal DNA and are given above.

(ii) Enzyme digestion. Digestion of amplified products was performed as directed by the manufacturer for the designated enzymes in volumes of 20 µl. Digestion products were analyzed by agarose (2% Metaphor agarose, FMC Corp., Rockland, Me.) gel electrophoresis and visualized after being stained with ethidium bromide.

Analysis of Type 6B PsaA.

Genomic DNA was partially digested by Sau3AI was ligated to BamHI-digested pUC18 and used to transform E. coli DH5α. Recombinant colonies were selected for resistance to ampicillin and the formation of white colonies in the presence of isopropyl-β-D-galactopyranoside (IPTG) and 5-bromo-4-chloro-3-indolyl-β-D-galactopyranoside. Colony immunoblot screening (using anti-PsaA MAb) of approximately 2,500 colonies yielded two positive clones, which were selected, purified, and rescreened by Western blot analysis using the same MAb. They both expressed a protein reactive with MAb to PsaA and which migrated in SDS-PAGE with the expected molecular mass of approximately 37 kDa. One was selected for continued study and was designated pSTR6.

Limited restriction enzyme analysis of DNA from the recombinant plasmid showed that the positive clone contained an insert that was 3.5 kb with sites for enzymes ClaI, EcoRI, and HindIII. To localize the PsaA coding region, the insert was double digested with SstI (multiple cloning site in vector) and HindIII. The resultant fragments were ligated into pUC18 and transformed into E. coli DH5α. This generated a recombinant containing an insert of ~1.3 kb in size. The resultant subclone pSTR6y, when analyzed by SDS-PAGE and Western blot using anti-PsaA MAb, was shown to express full length PsaA immuno-reactive protein.

The complete nucleotide sequence on both strands of the 1.3-kb insert was determined by cycle sequencing of the plasmid subclone using oligonucleotide primers complementary to the sequence. These were made as sequence information became available. The nucleotide sequence of the entire streptococcal insert is set forth in the Sequence Listing as SEQ ID NO:1. The single open reading frame (ORF) present, beginning at nucleotide (nt) 189 and ending at nt 1117, encodes the psaA gene sequence. This ORF is 930 nt long and when amplified and subcloned into vector systems such as pGEM (Promega, Madison, Wis.) and BAC-to-BAC™ expression system (Bethesda Research Laboratories, Gaithersburg, Md.) expresses full-length PsaA, reactive with anti-PsaA MAb antibodies. This ORF encodes a peptide of 309 amino acids with a deduced molecular weight of 34,598 and an isoelectric point of 5.23. Analysis of the peptide using the algorithm of Kyte and Doolittle (Kyte et al. 1982. "A simple method for displaying the hydropathic character of a protein." J. Mol. Biol. 157:105–132) shows that the peptide contains a major hydrophobic region of 20 amino acids which encodes a putative leader sequence. This leader contains the consensus sequence for signal peptidase cleavage (LXXC). Removal of this leader would result in a peptide of molecular mass 32,465 with a predicted isoelectric point of 4.97. A consensus sequence for a ribosomal binding site (Shine et al. 1974. "The 3'-terminal sequence of E. coli 16S ribosomal RNA: complementarity to nonsense triplets and ribosomal binding sites." Proc. Natl. Acad. Sci. USA 71:1324–1346) is located 5 nt upstream of the ATG start codon.

Comparison of the Serotype 6B Sequence with Streptococcal Homologs.

Comparison of the serotype 6B psaA nucleotide sequence ((Bilofsky et al. 1988. A GenBank genetic sequence database. Nucleic Acids Res. 16:1861–1864) GenBank accession number U53509) and its flanking regions with the previously published strain R36A psaA sequence (Sampson et al. 1994. "Cloning and nucleotide sequence analysis of psaA, the Streptococcus pneumoniae gene encoding a 37-kilodalton protein homologous to previously reported Streptococcus sp. adhesins." Infect. Immun. 62:319–324) shows the differences between the nucleotide sequences. The computed homology between the two sequences is 74%. Major areas of discord are in regions upstream and downstream of the ORF and in the initial 60 nt which encode the putative signal peptide. When the two PsaA coding sequences are compared the sequence homology increases to 78%. Serotype 6B sequence was also compared to the psaA DNA sequence for another vaccine serotype, serotype 2, which was recently submitted to GenBank by Berry and Paton (Accession number U40786). Computer analysis of these two sequences shows that they are very similar, with computed DNA homology percentages of 99% between the two psaA DNA sequences. There are eight single base differences between the two sequences.

A comparison of serotype 2 and 6B PsaAs shows almost complete identity: the computed similarity value is 99.3. The eight base difference at the nucleotide level translated into a difference at the peptide level of six amino acids with two of the changes resulting in conservative substitutions. Further analyses and comparisons of the serotype 6B sequence to the other five GenBank PsaA homologues from viridans Streptococci and E. faecalis (Fenno et al. 1989. "Nucleotide sequence analysis of a type 1 fimbrial gene of Streptococcus sanguis FW213." Infect. Immun. 57:3527–3533, Sampson et al. 1994. "Cloning and nucleotide sequence analysis of psaA, the Streptococcus pneumoniae gene encoding a 37-kilodalton protein homologous to previously reported Streptococcus sp. adhesins." Infect. Immun. 62:319–324, Ganeshkumar et al. 1991. "Nucleotide sequence of a gene coding for a salvia-binding protein (SsaB) from Streptococcus sanguis 12 and possible role of the protein in coaggregation with actinomyces." Infect. Immun. 59:1093–1099, Kolenbrander et al. 1994. "Nucleotide sequence of the Streptococcus gordonii PK488 coaggregation adhesin gene scaA and ATP-binding cassette." Infect. Immun. 62:4469–4480, and Lowe et al. 1995. "Cloning of an Enterococcus faecalis endocarditis antigen: homology with some adhesins from oral streptococci." Infect. Immun 63:703–706) revealed significant sequence similarity between them. Sequence identities were 81%, 81%, 77%, 82%, and 57%, respectively, for PsaA (S. pneumoniae strain R36A), SsaB (S. sanguis), FimA (S. parasanguis), ScaA (S. gordonii) and EfaA (E. faecalis). Additionally, all six sequences showed great similarity in organization. They have a hydrophobic leader peptide containing the prolipoprotein consensus sequence LXXC (for signal peptidase II cleavage) within the first 17–20 amino acids. This N-terminal leader sequence appears to represent the area of greatest variability. It is followed by a region of high similarity from amino acids 36–150. The region from 150 to 198 is a variable region and is followed by another conserved region (198–309).

PCR-RFLP Analysis of Chromosomal DNA from the 23 Serotype Strains in a 23-Valent Vaccine.

PCR-RFLP was used to examine the degree of conservation of the gene among 23 S. pneumoniae serotypes, representing the 23 serotypes in a 23-valent vaccine. Since previous attempts to amplify pneumococcal type strains with primers corresponding to strain R36A were unsuccessful primers for PCR were selected from N-terminal and C-terminal sequences of serotype 6B. Using primers complementary to serotype 6B, the psaA gene from all 23 serotypes and subtypes represented in the 23-valent vaccine was amplified from chromosomal DNA. A total of 10 enzymes were chosen that had restriction endonuclease digestion sites throughout the entire length of the serotype 6B psaA gene. Nine of the 10 enzymes gave identical patterns for all 23 psaA genes analyzed.

Cleavage with restriction enzyme Tsp509I was the one exception to those enzymes that generated identical patterns. Tsp509I has six sites within the gene and generates seven fragments upon digestion with sizes of 7, 30, 68, 146, 151, 166, and 362 bp. When these fragments are separated on 2% metaphor agarose gel, a five-band pattern can be seen (7- and 30-bp fragments are not seen on these gels because of their small size). For 21 of 23 serotypes this five-fragment enzyme pattern was obtained; but for strains of serotype 4 and 33F, the 146-bp fragment is absent and two new fragments appear flanking the 68-bp fragment making a total of seven bands. This increase in fragment number results from the presence of an extra Tsp509I site within the 146-bp fragment.

To ascertain the prevalence of this extra site, the Tsp509I patterns of 3 to 4 additional strains of each of 23 serotype strains (additional strains of serotype 2 and serotype 25 were not available) were analyzed. All strains analyzed were random clinical isolates from the United States that had been submitted to CDC for serotyping. The majority of the 80 strains were blood isolates; exceptions were 2 from cerebrospinal fluid, 2 from pleural fluid, and 1 each from the eye and nose. Of the strains analyzed, 10% had the extra Tsp509I site, resulting in the altered RFLP pattern. This modification was seen only in types 4, 8, 11F, and 33F. In an attempt to determine prevalence of this altered pattern, we analyzed the psaA gene from 8 additional strains of these 4 types for the Tsp509I variation (bringing the total to 11–12 for these 4 types). Table 1 summarizes the analyses of serotypes 4, 8, 11A, and 33F; it shows that the modified pattern is randomly present in 4 and 8, but is present in 11 of 12 strains of 11A and all strains of 33F. The occurrence of this pattern could not be correlated with geographic location or region of the United States since strains that showed variation came from diverse regions of the country. All strains of types 4, 8, 11A, and 33F were blood isolates except one 33F strain, which was a nasal isolate; thus the relevance of the site of isolation on prevalence of this modification could not be assessed.

TABLE 1

Screening of selected serotypes for additional Tsp509I restriction site

| Serotype | Ratio of serotypes with additional site to total no. of serotypes tested | | Total serotypes with unique patterns |
| --- | --- | --- | --- |
| | Expt. #1[a] | Expt. #2[b] | % Unique pattern |
| 4 | 1/3 | 3/9 | 33(4/12)[c] |
| 8 | 3/4 | 4/9 | 44(7/13) |
| 11A | 2/3 | 9/9 | 92(11/12) |
| 33F | 3/3 | 9/9 | 100(12/12) |

[a]Initial Tsp509I analysis which included survey of 2–3 strains each of all 23 vaccine types.
[b]Tsp509I analysis of more strains of types showing additional Tsp509I site.
[c]Shown in parenthesis is ratio of number with additional site to number tested.

This analysis discloses the cloning and sequencing of the gene encoding PsaA from *S. pneumoniae* serotype 6B and a subsequent analysis of the gene in the 23 pneumococcal polysaccharide vaccine serotypes. Sequence analysis revealed that the serotype 6B sequence and the previously published strain R36A were less similar than expected. The nucleotide sequence and its flanking regions were only 73% homologous to the original strain R36A psaA, with the actual PsaA coding sequences had a computed homology of 78%. Protein sequence similarity between the two sequences was only 81%. A comparison of the serotype 6B sequence with the newly submitted serotype 2 pneumococcal psaA (a vaccine serotype) gave computed DNA homology values of 99% and 98% protein sequence similarity. These values are evidence of the high sequence conservation for the gene within the vaccine serotypes. Moreover, when the deduced amino acid sequences of these two sequences were compared with other published sequences for PsaA homologues within the genus, large areas of similarity were evident for all five proteins. Similarity values within the group ranged from 57% to 82%.

The need for a *Streptococcus pneumoniae* vaccine candidate prompted us to clone and sequence the psaA gene from *S. pneumoniae* serotype 6B. The heterogeneity between the two pneumococcal psaA genes (6B and R36A) led us to examine the vaccine serotypes to determine the degree of diversity among strains. Primers homologous with the N terminus and C terminus of the serotype 6B sequence amplified all 23 of the vaccine serotypes. PCR-RFLP analysis using 10 different restriction enzymes representing 21 sites within the serotype 6B gene and shows only one area of diversity, which resulted in an additional Tsp509I site for a small number of strains.

This study demonstrates that the serotype 6B gene sequence is representative of the sequence found among the vaccine serotypes. Evidence for this includes the 99% DNA sequence identity between serotype 2 and serotype 6B and the uniform and identical restriction patterns covering the 21 sites examined in this study. It is clear that our earlier strain R36A psaA sequence represents a variant sequence seemingly not present in the serotypes that were analyzed here since we were unable to amplify them using primers to strain R36A psaA.

The more important aspect of this study, however, is that there is limited diversity among the vaccine serotypes analyzed. These are the serotypes that cause disease and thus, the ones against which prophylactic measures are needed. The lack of genetic diversity of psaA among these serotypes suggests that gene is highly conserved and is an excellent candidate for vaccine development.

The 37-kDa protein from serotype 22F was used to generate monoclonal antibodies 1B6E12H9, 3C4D5C7, 4E9G9D3, 4H5C10F3, 6F6F9C8, 8G12G11B10, which were analyzed for their ability to confer protection from infection by *Streptococcus pneumoniae*. Table 2 shows that of 5 monoclonal antibodies tested, one in particular gave efficient protection from subsequent *S. pneumoniae* challenge (8G12G11B1). The protection from *S. pneumoniae* was dose-responsive, demonstrating that the monoclonal antibody was responsible for the protection (Table 3).

TABLE 2

Passive protection of five (5) Anti-37 kDa murine monoclonal antibodies in an infant mouse model to *Streptococcus pneumoniae* serotype 6B.

| 37 kDa MAb Cell Line[a] | Bacteremia @ 48 h (%) | Death @ 48 h (%) | Death @ 14 d (%) |
|---|---|---|---|
| 1E7 . . . | 100 | 100 | 100 |
| 8G12 . . . | 100 | 0 | 20 |
| 4E9 . . . | 100 | 80 | 100 |
| 6F6 . . . | 100 | 60 | 100 |
| 1B6 . . . | 100 | 80 | 100 |

[a]Challenge does ($1.7 \times 10^3$ cfu) or 10x bacteremic dose 100% ($BD_{100}$). Five/mice group given 50 μg total antibody. All MAbs are IgG.

TABLE 3

Effect of a Second Dose on the Passive Protective Potential of the Anti-37 kDa Murine Monoclonal Antibody 8G12.

| Ab Dose Level (μg) | | Bacteremia @ 48 h | | Death @ 48 h (%) | Death @ 10 d (%) |
|---|---|---|---|---|---|
| Pre | Post[a] | % | Ave cfu/ml | | |
| 50 | — | 100 | $1.2 \times 10^4$ | 0 | 30 |
| 50 | 50 | 80 | $1.0 \times 10^4$ | 0 | 50 |
| 5 | — | 100 | $4.7 \times 10^4$ | 70 | 100 |
| 5 | 5 | 100 | $3.0 \times 10^4$ | 50 | 80 |
| — | — | 100 | $>10^5$ | 80 | 100 |

[a]All infant mice were challenged with 10x $BC_{100}$($2 \times 10^3$ cfu). Ab given 24 h prior to and 24 h after (post-) challenge. 10 mice/group.

---

What is claimed is:

1. A method of detecting the presence of the *Streptococcus pneumoniae* in a sample, comprising the steps of:
   a) contacting a sample suspected of containing *Streptococcus pneumoniae* with nucleic acid primers which selectively hybridize under stringent conditions to a unique portion of the nucleic acid set forth in SEQ ID NO:1 wherein said unique portion comprises at least 10 contiguous nucleotides of SEQ ID NO:1;
   b) amplifying the nucleic acid comprising a portion of the nucleic acid set forth in SEQ ID NO:1;
   c) detecting the presence of an amplification product, the presence of the amplification product indicating the presence of *Streptococcus pneumoniae* in the sample.

* * * * *

SEQUENCE LISTING

<160> NUMBER OF SEQ ID NOS: 4

<210> SEQ ID NO 1
<211> LENGTH: 1330
<212> TYPE: DNA
<213> ORGANISM: STREPTOCOCCUS PNEUMONIAE
<220> FEATURE:
<221> NAME/KEY: CDS
<222> LOCATION: (189)...(1115)

<400> SEQUENCE: 1

```
tactgcttca gttttgggac tctttattgg ctatagtttt aatgttgcgg caggttctag      60
tatcgtgctt acagctgcta gtttctttct cattagcttc tttatcgctc ccaaacaacg     120
atatttgaaa ctgaaaaata aacatttgtt aaaataaggg gcaaagccct aataaattgg     180 aggatcta atg aaa aaa tta ggt aca tta ctc gtt ctc ttt ctt tct gca      230
         Met Lys Lys Leu Gly Thr Leu Leu Val Leu Phe Leu Ser Ala
             1               5                  10 atc att ctt gta gca tgt gct agc gga aaa aaa gat aca act tct ggt      278
Ile Ile Leu Val Ala Cys Ala Ser Gly Lys Lys Asp Thr Thr Ser Gly
 15                  20                  25                  30 caa aaa cta aaa gtt gtt gct aca aac tca atc atc gct gat att act      326
Gln Lys Leu Lys Val Val Ala Thr Asn Ser Ile Ile Ala Asp Ile Thr
                 35                  40                  45 aaa aat att gct ggt gac aaa att gac ctt cat agt atc gtt ccg att      374
Lys Asn Ile Ala Gly Asp Lys Ile Asp Leu His Ser Ile Val Pro Ile
             50                  55                  60 ggg caa gac cca cac gaa tac gaa cca ctt cct gaa gac gtt aag aaa      422
Gly Gln Asp Pro His Glu Tyr Glu Pro Leu Pro Glu Asp Val Lys Lys
 65                  70                  75 act tct gag gct gat ttg att ttc tat aac ggt atc aac ctt gaa aca      470
Thr Ser Glu Ala Asp Leu Ile Phe Tyr Asn Gly Ile Asn Leu Glu Thr
             80                  85                  90 ggt ggc aat gct tgg ttt aca aaa ttg gta gaa aat gcc aag aaa act      518
Gly Gly Asn Ala Trp Phe Thr Lys Leu Val Glu Asn Ala Lys Lys Thr
 95                 100                 105                 110
```

```
gaa aac aaa gac tac ttc gca gtc agc gac ggc gtt gat gtt atc tac      566
Glu Asn Lys Asp Tyr Phe Ala Val Ser Asp Gly Val Asp Val Ile Tyr
                115                 120                 125 ctt gaa ggt caa aat gaa aaa gga aaa gaa gac cca cac gct tgg ctt      614
Leu Glu Gly Gln Asn Glu Lys Gly Lys Glu Asp Pro His Ala Trp Leu
        130                 135                 140 aac ctt gaa aac ggt att att ttt gct aaa aat atc gcc aaa caa ttg      662
Asn Leu Glu Asn Gly Ile Ile Phe Ala Lys Asn Ile Ala Lys Gln Leu
            145                 150                 155 agc gcc aaa gac cct aac aat aaa gaa ttc tat gaa aaa aat ctc aaa      710
Ser Ala Lys Asp Pro Asn Asn Lys Glu Phe Tyr Glu Lys Asn Leu Lys
    160                 165                 170 gaa tat act gat aag tta gac aaa ctt gat aaa gaa agt aag gat aaa      758
Glu Tyr Thr Asp Lys Leu Asp Lys Leu Asp Lys Glu Ser Lys Asp Lys
175                 180                 185                 190 ttt aat aag atc cct gct gaa aag aaa ctc att gta acc agc gaa gga      806
Phe Asn Lys Ile Pro Ala Glu Lys Lys Leu Ile Val Thr Ser Glu Gly
                195                 200                 205 gca ttc aaa tac ttc tct aaa gcc tat ggt gtc cca agt gcc tac atc      854
Ala Phe Lys Tyr Phe Ser Lys Ala Tyr Gly Val Pro Ser Ala Tyr Ile
        210                 215                 220 tgg gaa atc aat act gaa gaa gaa gga act cct gaa caa atc aag acc      902
Trp Glu Ile Asn Thr Glu Glu Glu Gly Thr Pro Glu Gln Ile Lys Thr
            225                 230                 235 ttg gtt gaa aaa ctt cgc caa aca aaa gtt cca tca ctc ttt gta gaa      950
Leu Val Glu Lys Leu Arg Gln Thr Lys Val Pro Ser Leu Phe Val Glu
    240                 245                 250 tca agt gtg gat gac cgt cca atg aaa act gtt tct caa gac aca aac      998
Ser Ser Val Asp Asp Arg Pro Met Lys Thr Val Ser Gln Asp Thr Asn
255                 260                 265                 270 atc cca atc tac gca caa atc ttt act gac tct atc gca gaa caa ggt     1046
Ile Pro Ile Tyr Ala Gln Ile Phe Thr Asp Ser Ile Ala Glu Gln Gly
                275                 280                 285 aaa gaa ggc gac agc tac tac agc atg atg aaa tac aac ctt gac aag     1094
Lys Glu Gly Asp Ser Tyr Tyr Ser Met Met Lys Tyr Asn Leu Asp Lys
        290                 295                 300 att gct gaa gga ttg gca aaa taagcctctg aaaaacgtca ttctcatgtg        1145
Ile Ala Glu Gly Leu Ala Lys
            305 agctggcgtt ttttctatgc ccacatttcc ggtcaaatca ttggaaaatt ctgactgttt   1205 cagatacaat ggaagaaaaa agattggagt atcctatggt aacttttctc ggaaatcctg  1265 tgagctttac aggtaaacaa ctacaagtcg gcgacaaggc gcttgatttt tctcttacta  1325 caaca                                                              1330

<210> SEQ ID NO 2
<211> LENGTH: 309
<212> TYPE: PRT
<213> ORGANISM: STREPTOCOCCUS PNEUMONIAE

<400> SEQUENCE: 2

Met Lys Lys Leu Gly Thr Leu Leu Val Leu Phe Leu Ser Ala Ile Ile
 1               5                  10                  15

Leu Val Ala Cys Ala Ser Gly Lys Lys Asp Thr Thr Ser Gly Gln Lys
            20                  25                  30

Leu Lys Val Val Ala Thr Asn Ser Ile Ala Asp Ile Thr Lys Asn
        35                  40                  45

Ile Ala Gly Asp Lys Ile Asp Leu His Ser Ile Val Pro Ile Gly Gln
```

```
                    50                  55                  60
Asp Pro His Glu Tyr Glu Pro Leu Pro Glu Asp Val Lys Lys Thr Ser
 65                  70                  75                  80

Glu Ala Asp Leu Ile Phe Tyr Asn Gly Ile Asn Leu Glu Thr Gly Gly
                 85                  90                  95

Asn Ala Trp Phe Thr Lys Leu Val Glu Asn Ala Lys Lys Thr Glu Asn
            100                 105                 110

Lys Asp Tyr Phe Ala Val Ser Asp Gly Val Asp Val Ile Tyr Leu Glu
        115                 120                 125

Gly Gln Asn Glu Lys Gly Lys Glu Asp Pro His Ala Trp Leu Asn Leu
    130                 135                 140

Glu Asn Gly Ile Ile Phe Ala Lys Asn Ile Ala Lys Gln Leu Ser Ala
145                 150                 155                 160

Lys Asp Pro Asn Asn Lys Glu Phe Tyr Glu Lys Asn Leu Lys Glu Tyr
                165                 170                 175

Thr Asp Lys Leu Asp Lys Leu Asp Lys Glu Ser Lys Asp Lys Phe Asn
            180                 185                 190

Lys Ile Pro Ala Glu Lys Lys Leu Ile Val Thr Ser Glu Gly Ala Phe
        195                 200                 205

Lys Tyr Phe Ser Lys Ala Tyr Gly Val Pro Ser Ala Tyr Ile Trp Glu
    210                 215                 220

Ile Asn Thr Glu Glu Gly Thr Pro Glu Gln Ile Lys Thr Leu Val
225                 230                 235                 240

Glu Lys Leu Arg Gln Thr Lys Val Pro Ser Leu Phe Val Glu Ser Ser
                245                 250                 255

Val Asp Asp Arg Pro Met Lys Thr Val Ser Gln Asp Thr Asn Ile Pro
            260                 265                 270

Ile Tyr Ala Gln Ile Phe Thr Asp Ser Ile Ala Glu Gln Gly Lys Glu
        275                 280                 285

Gly Asp Ser Tyr Tyr Ser Met Met Lys Tyr Asn Leu Asp Lys Ile Ala
    290                 295                 300

Glu Gly Leu Ala Lys
305

<210> SEQ ID NO 3
<211> LENGTH: 21
<212> TYPE: DNA
<213> ORGANISM: UNKNOWN
<220> FEATURE:
<223> OTHER INFORMATION: PRIMER

<400> SEQUENCE: 3
aggatctaat gaaaaaatta g                                              21

<210> SEQ ID NO 4
<211> LENGTH: 21
<212> TYPE: DNA
<213> ORGANISM: UNKNOWN
<220> FEATURE:
<223> OTHER INFORMATION: PRIMER

<400> SEQUENCE: 4
tcagaggctt attttgccaa t                                              21
```